United States Patent [19]

Elliott et al.

[11] Patent Number: 4,622,337
[45] Date of Patent: * Nov. 11, 1986

[54] 2,2-DIMETHYL-3-(2-HALOVINYL)CYCLO-PROPANE CARBOXLIC ACID ESTER PESTICIDES

[75] Inventors: Michael Elliott, Hertfordshire; Norman F. Janes, Bedfordshire; David A. Pulman, Hertfordshire, all of England

[73] Assignee: National Research Development Corporation, London, England

[*] Notice: The portion of the term of this patent subsequent to Aug. 7, 2001 has been disclaimed.

[21] Appl. No.: 612,807

[22] Filed: May 22, 1984

Related U.S. Application Data

[60] Division of Ser. No. 172,943, Jul. 28, 1980, Pat. No. 4,464,391, which is a continuation-in-part of Ser. No. 764,895, Feb. 2, 1977, abandoned, which is a continuation of Ser. No. 497,056, Aug. 13, 1974, Pat. No. 4,024,163, which is a continuation-in-part of Ser. No. 363,318, May 24, 1973, abandoned, and a continuation-in-part of Ser. No. 40,304, May 18, 1979, abandoned, and a continuation-in-part of Ser. No. 962,025, Nov. 20, 1978, abandoned.

[30] Foreign Application Priority Data

| May 25, 1972 | [GB] | United Kingdom | 24810/72 |
| May 25, 1972 | [GB] | United Kingdom | 24809/72 |
| Jun. 30, 1972 | [GB] | United Kingdom | 30838/72 |
| Dec. 21, 1972 | [GB] | United Kingdom | 59184/72 |
| Apr. 30, 1973 | [GB] | United Kingdom | 20539/73 |
| Aug. 15, 1973 | [GB] | United Kingdom | 39539/73 |
| Oct. 22, 1973 | [GB] | United Kingdom | 49098/73 |
| Jun. 13, 1974 | [GB] | United Kingdom | 26316/74 |
| Nov. 21, 1977 | [GB] | United Kingdom | 48454/77 |
| May 25, 1978 | [GB] | United Kingdom | 22638/78 |
| May 25, 1978 | [GB] | United Kingdom | 22639/78 |

[51] Int. Cl.[4] .................. A01N 53/00; C07C 69/743; C07C 69/747; C07D 307/54
[52] U.S. Cl. .................. 514/461; 514/471; 514/521; 514/531; 548/478; 549/473; 549/479; 549/488; 549/496; 549/499; 549/500; 549/501; 558/426; 560/124
[58] Field of Search ............... 549/473, 479, 488, 496, 549/499, 500, 501; 548/478; 560/124; 260/465 D; 424/274, 285, 304; 514/461, 471, 521, 531; 558/426

[56] References Cited

U.S. PATENT DOCUMENTS

| 3,465,007 | 9/1969 | Elliott | 549/499 X |
| 3,666,789 | 5/1972 | Itaya et al. | 560/124 |
| 3,758,504 | 9/1973 | Matsui et al. | 549/499 X |
| 3,847,944 | 11/1974 | Ohno et al. | 549/499 X |
| 3,857,863 | 12/1974 | Ohno et al. | 549/499 |
| 4,024,163 | 5/1977 | Elliott et al. | 424/285 |
| 4,464,391 | 8/1984 | Elliott et al. | 424/304 |

FOREIGN PATENT DOCUMENTS

1058309 2/1967 United Kingdom .

OTHER PUBLICATIONS

Farkas et al, Chem. Histy., vol. 52, (1958), pp. 688–694.

Primary Examiner—Richard L. Raymond
Attorney, Agent, or Firm—Cushman, Darby & Cushman

[57] ABSTRACT

New insecticides are of formula:

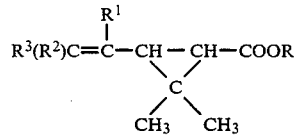

wherein $R^1$ represents hydrogen or a methyl group; $R^2$ represents hydrogen or a halogeno or lower alkyl group; $R^3$ represents hydrogen or a halogeno or carbo(-lower alkoxy) group which contains at least 2 carbon atoms in the lower alkoxy residue when $R^2$ represents methyl; with the proviso that (a) $R^2$ and $R^3$ each represent hydrogen only when $R^1$ represents methyl, (b) when $R^1$ and $R^3$ each represent hydrogen and $R^2$ represents alkyl, that alkyl group contains at least 2 carbon atoms and (c) when $R^3$ represents halogeno, $R^2$ represents hydrogen or halogeno; and R represents a group which forms insecticidal esters with chrysanthemic acid e.g. 5-benzyl-3-furylmethyl, 3-phenoxybenzyl, α-cyano-3-phenoxybenzyl. The esters are prepared by forming the ester linkage conventionally or by a Wittig reaction using a 3-formyl- or 3-acetyl-2,2-dimethyl cyclopropane carboxylic acid esterified with the desired residue or by an alkyl group which is subsequently converted to the desired residue.

12 Claims, No Drawings

2,2-DIMETHYL-3-(2-HALOVINYL)CYCLOPROPANE CARBOXLIC ACID ESTER PESTICIDES

This application is a division of copending application Ser. No. 172,943 filed July 28, 1980, now U.S. Pat. No. 4,464,391, which in turn is a continuation-in-part of copending Application Ser. No. 764,895 filed Feb. 2, 1977, now abandoned, which is itself a continuation of application Ser. No. 497,056 filed Aug. 13, 1974, now U.S. Pat. No. 4,024,163, which is itself a continuation-in-part of application Ser. No. 363,318 filed May 24, 1973, now abandoned. This application is also a continuation-in-part of application Ser. No. 40,304 filed May 18, 1979, now abandoned. This application is also a continuation-in-part of application Ser. No. 962,025 filed Nov. 20, 1978, now abandoned.

This invention relates to pesticides and more particularly to synthetic insecticides of the pyrethrin type, to their preparation, to compositions containing them and to the pesticidal use of the compounds and compositions.

For many years, research has been pursued in the field of synthetic analogues of the pyrethrins to discover synthetic substitutes having properties superior to those of the natural products. Ideally, synthetic analogues of the naturally occurring pyrethrins should compare well with or be superior to the natural products as regards level of toxicity to pests and mammals, pesticidal spectrum and known-down properties and, in addition, should offer ease of manufacture.

Since the discovery that the naturally occurring pyrethrins were esters of certain substituted cyclopropane carboxylic acids and substituted cyclopentenolones, the search for synthetic analogues concentrated initially on modifying the "alcohol" part of the ester molecule and later on modifying the "acid" part of the ester molecule or, in some cases, modifying both parts of the ester molecule. The naturally occurring esters are esters of chrysanthemic or pyrethric acids of the formula:

$$CH_3(X)C^*=CH-CH\underset{\underset{CH_3}{\diagup}\underset{CH_3}{\diagdown}}{\overset{\diagdown\;\diagup}{C}}CH-COOH \qquad I$$

where X represents a methyl group (chrysanthemic acid) or a carbomethoxy group (pyrethric acid).

We have now found that a high level of insecticidal activity and a particularly valuable combination of properties for controlling insects and other pests can be obtained in esters of 2,2-dimethyl-3-alkenyl cyclopropane carboxylic acid where the substitution on the 3-alkenyl side chain differs from that of all previously known pyrethrin-like esters, having high insecticidal activity and low mammalian toxicity. Certain esters of the invention also have exceptionally good photo stability.

Accordingly, the present invention provides esters of the general formula:

$$R^3(R^2)C=\overset{\overset{R^1}{|}}{C}-CH\underset{\underset{CH_3}{\diagup}\underset{CH_3}{\diagdown}}{\overset{\diagdown\;\diagup}{C}}CH-COOR \qquad II$$

wherein $R^1$ represents hydrogen or a methyl group; $R^2$ represents hydrogen or a halogeno or alkyl group; $R^3$ represents hydrogen or a halogeno or carboalkoxy group, said carboalkoxy group containing at least 2 carbon atoms in the alkoxy residue when $R^2$ represents methyl; with the proviso that (a) $R^2$ and $R^3$ each represent hydrogen only when $R^1$ represents methyl, (b) when $R^1$ and $R^3$ each represent hydrogen and $R^2$ represents alkyl, that alkyl group contains at least 2 carbon atoms and (c) when $R^3$ represents halogeno, $R^2$ represents hydrogen or halogeno; and R represents (a) hydrogen (or a salt or acid halide derivative of the acid) or an alkyl group, or (b) a group of formula:

$$\underset{\underset{R^8}{}}{\overset{\overset{D}{|}}{-CH}}\underset{O}{\overbrace{\phantom{xxx}}}\overset{R^7}{\phantom{x}}Z-Y \qquad III$$

or

[structure IV with $R^9$, $R^{10}$, $R^{11}$, $CH_2.R^{12}$]

or

[structure V with $X^1$, $X^2$, $X^3$, $X^4$, A/S, N—CH$_2$—]

or

[structure VI with D, CH—, Z$^3$, Z$^1_n$, Z$^2_n$]

or $$\underset{}{\phantom{x}}\!\!-CH_2-C\equiv C.CH_2- \qquad VIA$$

or $$\underset{}{\phantom{x}}\!\!-OCH_2.C\equiv C.CH_2- \qquad VIB$$

wherein Z represents O, S, CH$_2$ or CO, Y represents hydrogen or an alkyl, alkenyl or alkynyl group or an aryl of furyl group which is unsubstituted or substituted in the ring by one or more alkyl, alkenyl, alkoxy or halogeno groups, R$^7$ and R$^8$, which may be the same or different, each represent hydrogen or an alkyl, or alkenyl group, R$^9$ represents hydrogen or a methyl group, R$^{10}$ and R$^{11}$, which may be the same or different, each represent hydrogen or an alkyl group, R$^{12}$ represents an organic radical having carbon-carbon unsaturation in a position α to the CH$_2$ group to which R$^{12}$ is attached, A/S indicates an aromatic ring or a dihydro or tetrahydro analogue thereof, X$^1$, X$^2$, X$^3$ and X$^4$, which may be the same or different, each represent hydrogen, chlorine or a methyl group, Z$^3$ represents —CH$_2$— or —O— or —S— or —CO—, D represents H, CN or —C≡CH, Z$^1$ and Z$^2$, which may be the same or different, each represent chlorine or a methyl group and n=0, 1 or 2, with the proviso that R does not represent hydrogen (or an acid chloride derivative of the acid) or an ethyl or allethronyl group when R$^1$ represents hydrogen, R$^2$ and R$^3$ each represent chlorine and the compound is racemic.

The esters of the present invention where R represents a group of formula III, IV, V, VI, VIA or VIB are insecticidal esters having a valuable combination of properties for controlling insects and other pests.

The esters of the present invention where R represents alkyl are not insecticidal but are useful intermediates in the production of the insecticidal esters e.g. by transesterification. As will be discussed in more detail below, the new alkyl esters of the present invention can be prepared in that form by a Wittig synthesis and it is not necessary to convert the alkyl ester into the free carboxylic acid in order to produce the insecticidal esters of the invention. However, if desired, the alkyl esters can be converted into the free carboxylic acid, e.g. by hydrolysing the ester to give a salt and subsequently acidifying the salt.

The esters of the present invention where R represents alkyl and R$^3$=carboalkoxy are useful intermediates in the production of the insecticidal esters which can be converted by acid catalysis, e.g. using toluene-4-sulphonic acid in benzene, to the corresponding free carboxylic acid without affecting the carboalkoxy group R$^3$. As will be discussed in more detail below, the new alkyl esters of the present invention are prepared in that form by a Wittig synthesis and it is necessary to convert the alkyl ester into the free carboxylic acid in order to produce the insecticidal esters of the invention. This is best achieved selectively utilising a t-butyl ester (R=t-butyl). However, if desired, a t-butyl or other alkyl ester can be converted into the free carboxylic acid, by partial saponification but it is difficult to prevent saponification of the carboalkoxy group R$^3$ at the same time.

The insecticidal esters of the present invention may be regarded structurally as esters of a 3-substituted-2,2-dimethylcyclopropane carboxylic acid and an alcohol e.g. a benzyl alcohol, a furylmethyl alcohol, a cyclopentenolone or an α-cyano- or α-ethynyl-benzyl or α-cyano- or αethynyl-furylmethyl alcohol. While the esters may be conveniently described structurally in these terms, it will be appreciated and explained in more detail below, that the esters can be prepared by methods other than esterifying the acid with the alcohol and, in practice, often are.

So far as the various values of R$^2$ and R$^3$ are concerned, it is preferred that when these groups include alkyl, or carbo-alkoxy groups, the groups contain up to 6 carbon atoms, and, more particularly, up to 3 carbon atoms, methyl, ethyl, propyl, carbo-methoxy, carbo-ethoxy, and carbo-propoxy, being of particular interest. When R$^2$ and/or R$^3$ represents a halogeno group, it is preferably fluorine, chlorine or bromine. When R$^2$ and R$^3$ each represent halogeno they are preferably, but not necessarily the same halogen.

The esters of the present invention fall into various sub-classes structurally, depending primarily upon the nature of substituent R$^2$ and R$^3$. One sub-class of particular interest are those compounds where R$^1$ and R$^3$ each represent hydrogen and R$^2$ represents an alkyl group of at least two carbon atoms. We have now found that in this sub-class the highest toxicity to houseflies and mustard beetles of 5-benzyl-3-furylmethyl esters of 3-β-alkylvinyl-2,2-dimethylcyclopropane carboxylic acid is shown when the alkyl group is ethyl.

Further sub-classes of particular interest are those esters where R$^1$ and R$^3$ each are hydrogen and R$^2$ is chlorine or bromine and those compounds where R$^1$ is methyl and R$^3$ is hydrogen, and R$^2$ is hydrogen or an alkyl group containing up to 6 carbon atoms such as methyl, ethyl or propyl.

Another sub-class of particular interest are those compounds where R$^2$ represents hydrogen and R$^3$ represents a carboalkoxy group. These esters are esters of a demethyl pyrethric acid analogue which is devoid of the methyl substituent on the β-carbon atom of the 3-substituent. A further sub-class of considerable importance are those esters where R$^2$ represents methyl and R$^3$ represents a carboalkoxy group, where the alkoxy residue contains at least two carbon atoms. These esters are esters of pyrethric acid analogues which do not contain the carbomethoxy substituent on the β carbon atom of the 3-substituent.

Further sub-classes of particular interest are those esters where R$^2$ represents an alkyl group of at least two carbon atoms; again these esters are esters of a pyrethric acid homologue which does not contain the methyl substituent on the asterisked carbon atom of formula I. In these esters, R$^3$ may represent the carbomethoxy group (which is present in pyrethric acid) or a higher homologue thereof.

A useful group of active insecticidal esters of the invention are those where R$^1$ represents hydrogen and R$^2$ and R$^3$ each represents a halogeno group. Certain esters of the 3-dihalovinyl acids are also of particular value because of their greater light stability than the corresponding chrysanthemates. These are therefore suitable for use against pests of agricultural crops in sunlight, as well as in domestic and horticultural situations.

A further halogenated sub-class of interest are those esters where R$^1$ represents hydrogen, R$^2$ represents halogeno and R$^3$ represents carboalkoxy. The acid residues in these esters are analogues of pyrethric acid where the methyl substituent on the β-carbon atom of the 3-substituent is replaced by halogeno and homologues of these acids where the carbomethoxy group is replaced by a carboalkoxy group containing at least 3 carbon atoms. The halogen is preferably chlorine or bromine and the carboalkoxy group is preferably carbomethoxy, -ethoxy or -n-propoxy.

Preferred esters of the present invention include those which are structurally esters of a 2,2-dimethyl-3-substituted cyclopropane carboxylic acid where the 3-substituent is:

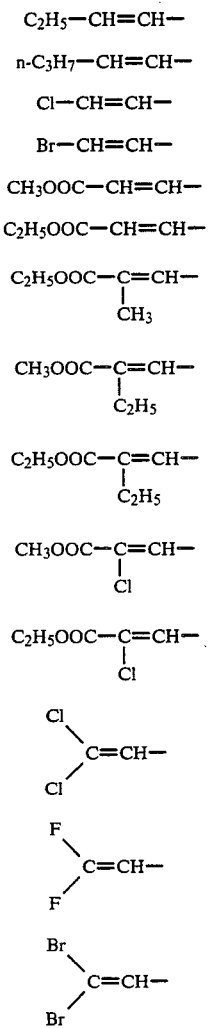

$C_2H_5-CH=CH-$ $n-C_3H_7-CH=CH-$ $Cl-CH=CH-$ $Br-CH=CH-$ $CH_3OOC-CH=CH-$ $C_2H_5OOC-CH=CH-$ $C_2H_5OOC-\underset{CH_3}{\underset{|}{C}}=CH-$ $CH_3OOC-\underset{C_2H_5}{\underset{|}{C}}=CH-$ $C_2H_5OOC-\underset{C_2H_5}{\underset{|}{C}}=CH-$ $CH_3OOC-\underset{Cl}{\underset{|}{C}}=CH-$ $C_2H_5OOC-\underset{Cl}{\underset{|}{C}}=CH-$ $\underset{Cl}{\overset{Cl}{\diagdown}}C=CH-$ $\underset{F}{\overset{F}{\diagdown}}C=CH-$ $\underset{Br}{\overset{Br}{\diagdown}}C=CH-$ When the esters of the present invention are alkyl esters, it is preferred that the alkyl group be one containing up to 6 carbon atoms and we have found that methyl, ethyl and tertiary butyl esters are amongst those which can be readily prepared by our synthetic methods.

When the ester is one structurally derived from a furylmethyl alcohol it is preferred that the furylmethyl alcohol be one of the 3-furylmethyl alcohols described in British Patent Specification No. 1,168,798. In the furylmethyl alcohols, and particularly in the 3-furylmethyl alcohols, it is preferred that $R^7$ and $R^8$ each represent hydrogen or groups containing up to 4 carbon atoms, particularly a methyl group and that Y represents a phenyl group which is unsubstituted or substituted in the ring by a group containing up to 4 carbon atoms, e.g. methyl or methoxy, or by chlorine, and $Z=CH_2$, and $D=H$. Analogues of these compounds where $Z=O$, S or CO and $D=CN$ or $C\equiv CH$ can also be used. Other compounds of interest are those where Y represents a hydrogen atom, an alkyl group containing up to 4 carbon atoms, an alkenyl group containing up to 4 carbon atoms, e.g. vinyl, an alkadienyl group containing up to 4 carbon atoms or an alkynyl group e.g. propargyl or a furyl group.

Specific alcohols of this category, from which the esters of the invention are structurally derivable, include 5-benzyl-3-furylmethyl alcohol, 5-benzyl-2-methyl-3-furylmethyl alcohol, 5-benzylfurfuryl alcohol, 4-benzyl-5-methyl-furfuryl alcohol, 5-p-xylyl-furfuryl alcohol, 2,4,5-trimethyl-3-furylmethyl alcohol, 4,5-dimethylfurfuryl alcohol, 5-phenoxy- and 5-benzoyl-3-furylmethyl alcohol and α-cyano- and αethynyl- -5-benzyl-, -5-benzoyl- and -5-phenoxy-3-furylmethyl alcohol.

The cyclopentenolones from which the esters of the invention are structurally derivable are those unsubstituted in the 3-position or those substituted in the 3-position by a methyl group, ($R^9=H$ or $CH_3$).

The cyclopentenolones unsubstituted in the 3-position are described in British Patent Specification No. 1,305,025. Some of these alcohols are the 3-demethyl analogues of the alcohols from which the naturally occurring pyrethrins are derived. In the present invention, it is preferred that $R^{10}$ and $R^{11}$ each represent hydrogen, methyl or ethyl and $R^{12}$ represents an aryl group such as a phenyl group or a phenyl group substituted by a halogeno or alkyl or alkoxy substituent, of 1 to 4 carbon atoms, for example tolyl, xylyl, p-chlorophenyl or p-methoxyphenyl. $R^{12}$ may also represent a 2- or 3-furyl group or an alkenyl group such as a vinyl, prop-1-enyl or buta-1,3-dienyl group.

When the esters of the invention are structurally derivable from the cyclopentenolones which are substituted in the 3-position by the methyl group, ($R^9=$methyl), the esters may be derived from allethrolone ($R^{10}=R^{11}=H$, $R^{12}=$vinyl), pyrethrolone ($R^{11}=R^{11}=H$, $R^{12}=$buta-1,3-dienyl), cinerolone ($R^{10}=R^{11}=H$, $R^{12}=$prop-1-enyl), jasmolone ($R^{10}=R^{11}=H$, $R^{12}=$but-1-enyl) or furethrolone ($R^{10}=R^{11}=H$, $R^{12}=$2-furyl).

When the esters of the invention are phthalimidomethyl esters where R is of formula V, they may be phthalimido, dihydrophthalimido or tetrahydrophthalimido-methyl esters where the phthalimido, dihydrophthalimido or tetrahydrophthalimido residue is one described in British Patent Specification Nos. 985,006, 1,052,119 or 1,058,309. 3,4,5,6-Tetrahydrophthalimidomethyl esters are of particular interest.

When the esters of the invention are those where R is of formula VI, it is preferred that they be 3-benzylbenzyl esters, 3-benzoylbenzyl esters or 3-phenoxybenzyl esters although each of the rings may be substituted by up to 3 chloro and/or methyl groups. Other esters of particular interest where R is of formula VI are those where $Z^3$ represents O or $CH_2$ and D represents $-CN$ or $-C\equiv CH$, e.g. esters of α-cyano- or α-ethynyl-3-phenoxybenzyl alcohol and of α-cyano- or α-ethynyl-3-benzylbenzyl alcohol and esters of α-cyano- or α-ethynyl- -3-benzoylbenzyl alcohol.

The compounds of the present invention exhibit geometrical and optical isomerism and consequently may be prepared in optically active forms which may subsequently be mixed together or as racemic mixtures which may subsequently be resolved into optically active forms. In addition, optically active forms or racemic mixtures can be separated into the individual diastereoisomers. In addition to the geometrical isomerism that results from the configuration of the substituents on the cyclopropane ring with respect to one another and the ring, there is also the possibility of geometrical isomerism in the side chain on position 3 when $R^1$, $R^2$ and $R^3$ are such that the unsaturated side-chain is unsymmetrically substituted. In the α-cyano- and α-ethynyl compounds (D=CN or C≡CH), there is a further possibility of optical isomerism and the compounds envisaged include esters of both the racemic mixture and of the separate isomers resulting from the asymmetry at the carbon atom bearing the D group. The various optical and geometrical isomers of the esters of the invention usually have different insecticidal toxicities and knockdown potency.

The compounds of formula II can exist in the form of geometrical isomers depending upon whether the hydrogen atoms carried at $C_1$ and $C_3$ of the cyclopropane ring are in the cis or trans relationship. Because of the unsymmetrical substitution at $C_1$ and $C_3$ on the cyclopropane ring, each cis isomer can exist in one of two optically active forms and each trans isomer can exist in one of two optically active forms. When the absolute configuration at $C_1$ of compounds of formula II is the same as that at $C_1$ in (+)-trans chrysanthemic acid, the absolute configuration of $C_1$ in compound II is designated 1R. The absolute configuration of $C_3$ in compounds of formula II cannot vary independently of the $C_1$ configuration in a compound having specified geometrical configuration and, for a dihalo compound having trans configuratio and R configuration at $C_1$, strict application of the sequence rule (Cahn, R. S. Ingold C. and Prelog V. Angew. Chem. Int. Ed. 5, 385 (1966)) requires the designation S to be applied at $C_3$. However, application of the same sequence rule to the same $C_3$ centre in (+)-trans chrysanthemic acid requires that centre to be designated R, even though it is directly related in absolute configuration to the configuration designated S in dihalo compounds of formula II. This is because the nature o the substitution at $C_3$ is different in (+)-trans chrysanthemic acid from that of dihalo compounds of formula II. However, because the specification of the geometrical configuration and the absolute configuration at $C_1$ fixes the $C_3$ configuration absolutely, and to avoid possible confusion arising from the fact that different compounds of the same series may otherwise require sometimes R, sometimes S designations of the configuration at $C_3$, we have proposed the nomenclature (1R)-trans for such compounds as this provides sufficient information to determine the absolute configuration of the cyclopropane ring part of the molecule.

Similar considerations have resulted in our designating compounds having the same absolute configuration as (+)-cis chrysanthemic acid as (1R)-cis compounds. In cases where we have dealt with compounds having the same configuration as (−)-trans or (−)-cis chrysanthemic acid, we are applying the designations (1S)-trans and (1S)-cis respectively.

Apart from the (1R)-cis, (1R)-trans, (1S)-cis and (1S)-trans compounds, esters derived from (±)-trans and (±)-cis acids (now designated (1RS)-trans and (1RS)-cis respectively) are also of interest, as well as mixtures of (1R)-trans and (1R)-cis and (1RS)-trans and (1RS)-cis with varying proportions of the cis and trans isomers.

There is as mentioned above a further possible site of asymmetry in compounds of formula II, that is when the R group is of formula III or VI and substituent D on the α-carbon is other than hydrogen. These compounds of formula II can exist in forms having the absolute (R)-configuration or in forms having the absolute (S)-configuration at this α-carbon atom.

When $R^1$ represents hydrogen and $R^2$ and $R^3$ each represent bromine, then an unexpected level of selectivity in combatting certain pests is obtained with those compounds where the configuration about the cyclopropane ring is cis and R represents α-cyano-3-benzoylbenzyl. This unexpected selectivity exists in relation to the control of certain lepidopterous pests *Ephestia kuhniella* which is a stored product pest. The Ephestia frequently carry a hymenopterous parasite called *Venturia canescens*. An ideal agent to control the lepidopterous stored products pest should exhibit selectivity towards killing the lepidopterous pest over killing the Venturia parasite. If such a selective control agent were to be used, which were to kill the lepidopterous pest but leave the parasite unaffected, then in the event of a subsequent infestation of the stored product by further lepidopterous pest, the Venturia remaining from the previous infestation would be able to prevent the development of the subsequent infestation of lepidopterous pests and so prolong the period during which the stored product could be kept free of infestation on the basis of a single treatment with the control agent. It has been found that the types of compound identified above do exhibit such selectivity. A particularly valuable selectivity is observed in compounds of this type when the ester is in the form of a substantially pure optical isomer with respect to the cyclopropane ring and the ester has (R)-configuration at $C_1$ of the cyclopropane ring as is illustrated in Example 40.

The insecticidal esters of the present invention may be prepared by esterification involving the reaction of an alcohol or derivative thereof of formula R-Q e.g. of formula VII, VIII or VIIIA, and a cyclopropane carboxylic acid or derivative thereof of formula IX,

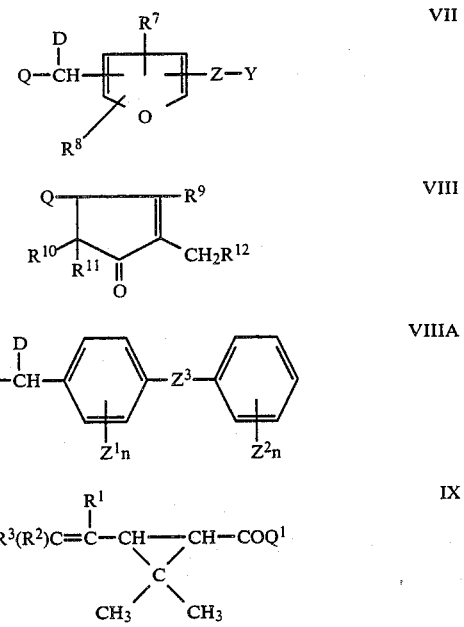

where Q and $COQ^1$ are functional groups or atoms which will react together to form an ester linkage and R, $R^1$, $R^2$, $R^3$, $R^7$, $R^8$, $R^9$, $R^{10}$, $R^{11}$, $R^{12}$ and D, Z, $Z^1$, $Z^2$, $Z^3$, Y and n are as defined above.

It is usually convenient in practice either to react the acid or acid halide with the alcohol ($COQ^1$=COOH or CO—halide and Q=OH) or to react a halogeno compound (Q=halogen) with a salt of the carboxylic acid ($COQ^1=COO^\ominus M^\oplus$ where M is, for example, a silver or triethylammonium cation).

For reasons which will shortly be described, reactant IX normally becomes available initially in the form of a lower alkyl ester, ($COQ^1=COO$ alkyl) where the alkyl group contains 1 to 6 carbon atoms and consequently, a particularly convenient way of preparing the insecticidal esters of the invention, except where $R^3$ is carboalkoxy, is to subject the alkyl ester of formula IX to transesterification using an alcohol ROH, e.g. in the presence of a basic catalyst. When the alkyl ester contains a base sensitive group, e.g. $R^3$=carboalkoxy, base catalysed transesterification is undesirable and can be avoided by preparing a t.-butyl ester which can be converted into the free acid by acid catalysed decomposition and the free carboxylic group esterified directly or via a salt or halide.

The esters of the present invention can also be prepared by reaction between a phosphorane or ylide of formula X and an ester of 2,2-dimethyl cyclopropane carboxylic acid substituted at the 3-position by an acetyl group or an aldehyde group of formula XI:

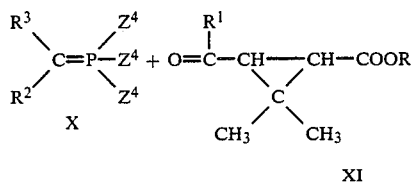

In formulae X and XI $R^1$, $R^2$, $R^3$ are as defined above and R is a group as defined above which will not interfere in the Wittig reaction and $Z^4$: which in principle can represent any organic radical, will normally be a phenyl radical since the stability of the trisubstituted phosphorus oxide which is formed as the by-product in the reaction is particularly high and this favours completion of the reaction between the phosphorane X and the aldehyde or ketone XI. Alternatively, the phosphorane X can be replaced by another equivalent Wittig reagent or other ylide.

Esters of the present invention where $R^1$ represents hydrogen can be prepared by reaction with an aldehyde of formula XI while esters of the invention where $R^1$ represents methyl can be prepared by reaction of a 3-acetyl compound of formula XI. The phosphorane X and aldehyde or ketone XI are preferably reacted in substantially equimolar proportions, conveniently in the solvent in which the phosphorane itself has been prepared. As will be discussed in more detail below, this may be an aromatic hydrocarbon such as benzene or a polar solvent such as dimethyl sulphoxide or a chlorinated hydrocarbon such as dichloromethane. The product can be improved if reaction is carried out in an inert atmosphere e.g. under nitrogen. The reaction between the phosphorane and aldehyde or ketone is normally quite rapid and the desired ester can be recovered from the reaction mixture after a reaction time of less than 1 hour although reaction times of up to 24 hours have been used. The desired ester can be recovered from the reaction product by solvent extraction e.g. with diethyl ether or petroleum ether.

The phosphorane of formula X where neither $R^2$ nor $R^3$ represent halogen can be prepared from the corresponding phosphonium salt which in turn can be prepared by reacting the appropriately substituted methyl halide with a triorganophosphine in accordance with the following reaction scheme:

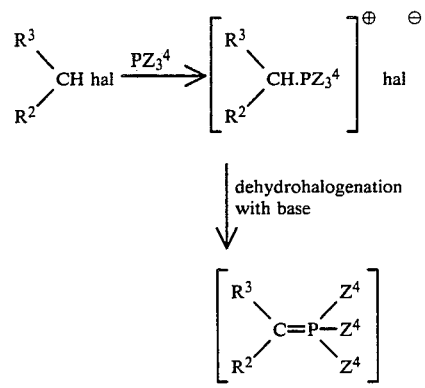

The flexibility of the product synthetic method results from the fact that the initial starting material is the substituted methyl halide $R^3(R^2)CH$ hal and the availability of whole series of such substituted halides permits the production of whole series of 2,2-dimethyl cyclopropane carboxylic acids which are substituted in the 3-position by various groups which have previously been difficult or impossible to prepare. In the above-mentioned synthesis of the phosphorane, it is convenient to start with a substituted methyl bromide which is reacted with triphenylphosphine to give the corresponding triphenylphosphonium bromide and subsequently converting the phosphonium salt to the phosphorane or ylide which can be designated by the formula given above. The conversion of the phosphonium salt to the phosphorane can be brought about by treating the phosphonium salt with an alkali metal amide or alkali metal methyl sulphinyl methide ($\ominus CH_2.SO.CH_3 M^\oplus$). For example, sodamide can be prepared by reacting sodium in liquid ammonia and the reaction carried out in the presence of the excess ammonia as the liquid medium. At the end of the reaction, the liquid ammonia can be allowed to evaporate and the phosphorane taken up into an organic solvent such as benzene and the subsequent reaction with aldehyde or ketone XI carried out in this organic solvent. Alternatively, dimethyl sulphoxide can be reacted with sodium hydride to give sodium methyl sulphinyl methide and the production of the phosphonium salt carried out using this reagent and, following formation of the phosphorane, the subsequent reaction with the aldehyde or ketone XI can be carried out in the same reaction medium.

When $R^3$=carboalkoxy, the conversion of the phosphonium salt to the phosphorane can be brought about by treating the phosphonium salt with an alkali metal amide in liquid ammonia or in aqueous alkali metal hydroxide solution, e.g. 5% NaOH. The liberated phosphorane can be filtered from the solution and subsequently reacted with the aldehyde XI in a suitable solvent e.g. $CH_2Cl_2$.

Phosphoranes where $R^3$ represents carboalkoxy and $R^2$ represents hydrogen or methyl can be prepared by the above described procedures using a haloacetate or α-halopropionate alkyl ester as the substituted methyl halide but this synthesis is not entirely satisfactory for the preparation of phosphoranes of this type where $R^2$ represents an alkyl group of 2 or more carbon atoms. For such higher homologues, a phosphorane where $R^3$ represents hydrogen and $R^2$ represents the desired alkyl group is first prepared as an intermediate by the procedures described above starting from an alkyl halide of at least 3 carbon atoms and this intermediate phosphorane is then reacted with the appropriate alkyl chloroformate ester to introduce the desired carboalkoxy group.

Phosphoranes where $R^2$ and/or $R^3$ represent halogen can be prepared by simple modifications of the above described synthesis.

When $R^2$ and $R^3$ each represent halogen, a carbon tetrahalide can be used in place of the substituted methyl halide and the reaction proceeds in accordance with the equation:

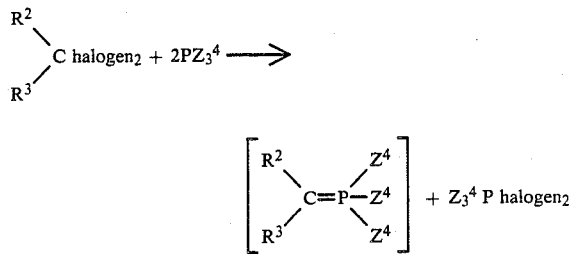

the dehydrohalogenation of the quaternary phosphonium halide proceeding spontaneously.

Halogenated phosphoranes can also be prepared by halogenating an unhalogenated phosphorane, itself obtained by the above described procedures in accordance with the following reaction scheme:

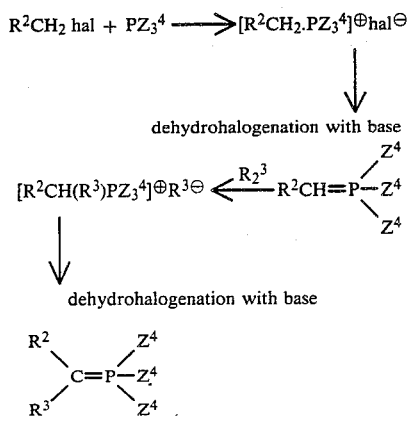

where hal=halogen, $R^3$=halogen and $R^2$ is as defined above.

We have found that it is desirable that the carboxyl group in the aldehyde or ketone reactant XI be esterified as a lower alkyl ester in order to achieve the most satisfactory results in the reaction with the phosphorane X. This means that the alkyl esters of the present invention are produced directly and, since it is possible to convert these alkyl esters into the insecticidal esters of the invention, except those containing a base sensitive group, e.g. $R^3$=carboalkoxy, by a simple base catalysed transesterification reaction, it is not necessary to convert the alkyl esters of the invention into the corresponding acid in order to produce the insecticidal esters. However, indirect conversion of the alkyl esters to the insecticidal esters is possible in accordance with the present invention and, when operating in accordance with this embodiment, the carboalkoxy group in the ester of formula II can be converted by conventional hydrolysis into the corresponding free carboxylic acid group going, via the alkali metal or other salt for instance, and this carboxylic acid can be directly esterified as described above or alternatively can be converted first into an acid halide e.g. the chloride and this acid halide converted into an ester by reaction with an appropriate alcohol of formula ROH as described above.

In the case where R is a t.-butyl group, the alkyl ester can be converted into the free acid by heating with a small amount of toluene-4-sulphonic acid. This reaction can be carried out in benzene and the resulting carboxylic acid converted to the acid chloride in the benzene solution without isolation.

In the synthetic methods described so far, alkyl esters of the invention are prepared by a Wittig reaction between a phosphorane X and an alkyl ester of a carbonyl compound XI and the resulting alkyl ester of the invention converted to an insecticidal ester by transesterification or via the free acid and acid chloride which is subsequently reesterified e.g. with 5-benzyl-3-furylmethyl alcohol. It is usually most convenient to operate in this manner but is not essential to do so and a practical alternative is to produce the insecticidal ester directly by reacting the phosphorane X with a carbonyl compound of formula XI where R represents a group of formula III, IV, V, VI, VIA or VIB as defined above.

Such carbonyl compounds of formula XI may be prepared by the synthetic methods described above but converting the group R from an alkyl group to a group of formula III, IV, V, VI, VIA or VIB before the Wittig reaction instead of after the Wittig reaction as described above.

Carbonyl compounds of formula IX can be prepared by ozonolysis of the corresponding ester of chrysanthemic acid, when oxygenation of the double bond in the isobutenyl side chain occurs. Thus, provided R does not contain a group degradable under ozonolysis conditions, the required carbonyl compound XI for this alternative method can be obtained directly by ozonolysis of the chrysanthemate and the ozonolysed chrysanthemate XI used in the Wittig reaction to give the insecticidal ester. Some furan containing compounds are degraded under ozonolysis conditions so the 5-benzyl-3-furylmethyl ester of caronaldehyde cannot be obtained by direct ozonolysis of the corresponding chrysanthemate (it must be obtained in two stages via an alkyl ester of caronaldehyde) but a 3-phenoxybenzyl ester can be so treated.

Acids of the general formula IX ($COQ^1$=COOH) where $R^1$=$R^3$=H and $R^2$=an alkyl group containing at least two carbon atoms can be prepared by reaction between 2-ethynyl-3,3-dimethyl cyclopropane carboxylic acid and an appropriate alkyl halide in the presence of an alkali metal followed by catalytic semihydrogenation. Acids where $R^2$=$R^3$=Cl can be prepared by reacting ethyl diazoacetate with 1,1-dichloro-4-methyl-penta-1,3-diene and converting the ethyl ester to the acid.

Alcohols and halides of formula VIII are described in British Patent Specification No. 1,305,025.

Alcohols of formula VII or VIIIA where D represents CN or C≡CH can be prepared by conventional methods from the corresponding aldehydes. Thus, a furaldehyde or benzaldehyde can be reacted with (a) HCN, conveniently generated in situ from KCN and acid, when addition of HCN occurs forming the cyanhydrin or (b) an alkali metal acetylide in liquid ammonia.

Alcohols of formula ROH where R is a group of formula VI where D represents hydrogen may be prepared by reduction of the corresponding acids or esters e.g. with a hydride, or by conversion of the corresponding halide to an ester e.g. by reaction with sodium acetate, followed by hydrolysis of the ester, or by reaction of formaldehyde with a Grignard reagent derived from the corresponding halide. The halides of formula R-halogen where R is a group of formula VI where D represents hydrogen can be prepared by halomethylation of the compound:

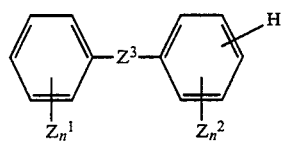

or side chain halogenation of:

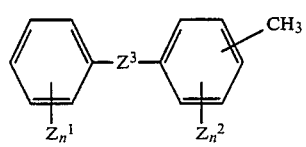

The benzolybenzyl alcohols and derivatives thereof may be prepared from 3-methyl-benzophenone. The benzophenone is first brominated in the side chain using N-bromosuccinimide. This bromination gives a mixture of compounds which are monobrominated and dibrominated in the methyl side chain. This mixture of monobromo and dibromo compounds may then be hydrolysed, under acid or alkaline conditions, e.g. by refluxing with alcoholic KOH, when the monobromo methylbenzophenone is converted directly into the desired 3-benzolybenzyl alcohol while the dibromo methyl compound is converted into 3-benzoylbenzaldehyde which may be separated from the alcohol by fractionation. The benzaldehyde may then be reacted with HCN under the conventional conditions for this reaction when the aldehyde is converted into α-cyano-3-benzoylbenzyl alcohol. This last-mentioned reaction produces the α-cyano compound as a racemic mixture.

Normally, the primary or secondary alcohol prepared by the synthesis described above is used directly in the esterification with the cyclopropane-carboxylic acid to produce esters of the invention. However, if it is desired to use another esterification technique, the primary or secondary alcohol may be converted into another esterifiable derivative by methods known per se.

It is also possible to produce individual isomers of the present invention by first preparing isomer mixtures of the present invention by the esterification techniques described above and then subjecting the isomer mixture to thin layer chromatography or to high pressure liquid chromatography which enables the individual isomers to be eluted sequentially from, for example, silica gels, using solvent mixtures such as hexane/diethyl ether.

One or more of the insecticidal esters of the invention may be formulated with an inert carrier or diluent to give insecticidal compositions and these may be prepared, for example, in the form of dusts and granular solids, wettable powders, mosquito coils and other solid preparations or as emulsions, emulsifiable concentrates, sprays and aerosols and other liquid preparations after the addition of the appropriate solvents, diluents and surface active agents. The compositions usually contain 0.0001 to 95% by weight, preferably up to 50% by weight of the active compound.

Pyrethrum synergists such as piperonyl butoxide, Sesamex or tropital, may be added to these compositions. Certain insecticidal esters of the invention show significant superiority over structurally similar esters e.g. chrysanthemates or pyrethrates, in the ability to respond to synergists and many esters of the invention have a synergistic factor several times greater than those exhibited by other synthetic esters. Many of the esters derived from acids of the present invention are much more stable to light than those of previously known acids, and dihalovinyl esters are especially favoured in this connection.

The insecticidal compositions may also include known synthetic pyrethrins to improve kill and/or knockdown or to synergise the activity of the known pyrethrin and/or that of the synthetic pyrethrins of the invention.

The new esters of the invention or insecticidal compositions containing them may be used for killing insects or controlling the level of insects on a domestic or agricultural scale by treating the insects themselves or an environment susceptible to insect attack with the compounds or compositions. The compounds of the invention also exhibit valuable acaricidal properties, particularly against cattle tick.

The following Examples are given to illustrate the present invention (temperatures are in °C., refractive indices are measured at 20° C. Unless otherwise indicated, the hydrogen atoms at $C_1$ and $C_3$ of the cyclopropane ring are in the trans-relationship to one another).

EXAMPLE 1 n-Pentyl triphenylphosphonium iodide (9.5 g., 0.02M), prepared by reaction of n-pentyl iodide with triphenylphosphine, was added slowly, under nitrogen, to sodamide [0.7 g. sodium (0.03M) in liquid ammonia (130 ml.)]. The mixture was stirred for 0.5 hours and the ammonia allowed to evaporate (2 hours). Benzene (130 ml.) was added and the mixture refluxed, under nitrogen, for 0.5 hours, allowed to cool and the supernatant liquid containing the phosphorane decanted off under nitrogen.

The phosphorane solution was added dropwise, under nitrogen, to a stirred solution of methyl (1R)trans caronaldehyde (1.0 g., 0.0064M) (from ozonolysis of methyl ester of (1R)-trans-chrysanthemic acid) in dry benzene (15 ml.). The addition was completed in 10 minutes and the solution was stirred for a further 0.5 hours. The solution was evaporated, the residue dissolved in diethyl ether, the organic solution washed with water and dried. Evaporation yielded a colourless mixture which was further extracted with petroleum ether (60°–80°), evaporation of which yielded a colourless liquid b.p. 107°–109°/5 mm., yield (1.07 g., (80%), $n_D$ 1.4622) which was identified by NMR spectroscopy as 2,2-dimethyl-3-(hex-1-enyl)-cyclopropane carboxylic acid methyl ester. (Compound C′).

EXAMPLE 2

The procedure described in Example 1 was repeated replacing the n-pentyl iodide with equivalent amounts of n-propyl iodide or n-butyl bromide, to give alkyl esters of the invention of formula II and of refractive index as indicated below:

| Compound | $R^2$ | $R^3$ | $R^1$ | R | $n_D$ |
|---|---|---|---|---|---|
| A' | $C_2H_5$ | H | H | $CH_3$ | 1.4581 |
| B' | n-$C_3H_7$ | H | H | $CH_3$ | 1.4572 |

In Compound A', the 3-but-1-enyl substituent is in the trans relationship to the cyclopropane ring. Its (1R)-cis-isomer (in free acid form) was made by the following procedure. (In both Compound A' and its cis isomer, the configuration around the ethylenic double bond in the 3-substituent is cis.)

n-Propylidene phosphorane [prepared by reacting the corresponding phosphonium iodide (7 g.) with sodamide, (sodium (0.7 g.)/liquid ammonia (150 ml.))] in dry benzene (100 ml.) was added dropwise, with stirring, to a solution of the internal hemi-acetal of cis-3-formyl-2,2-dimethyl-cyclopropane carboxylic acid (0.7 g.) (French Patent Specification No. 1,580,475) in benzene (10 ml.), under nitrogen. The benzene was evaporated off and the residue dissolved in methylene chloride (75 ml.) and washed with water and sodium carbonate solution. Acidification of the carbonate extract yielded an acid which was extracted with methylene chloride, dried ($Na_2SO_4$), and evaporated to give (1R)-cis-3-but-1-ene-2,2-dimethyl-cyclopropane carboxylic acid (0.7 g.). (Compound A' cis).

EXAMPLE 3

The procedure described in Example 1 was repeated replacing the methyl trans-caronaldehyde by an equivalent weight of ethyl (1RS)-cis-trans-3-acetyl-2,2-dimethylcyclopropane carboxylate and replacing the n-pentyl iodide by methyl iodide, ethyl iodide, n-propyl iodide, or n-butyl bromide to give the alkyl esters of formula II as indicated below having the following refractive index:

| Compound | $R^2$ | $R^3$ | $R^1$ | R | $n_D$ |
|---|---|---|---|---|---|
| F' | H | H | $CH_3$ | $C_2H_5$ | 1.4469 |
| G' | (1) $CH_3$ | H | $CH_3$ | $C_2H_5$ | 1.4570 |
| H' | (2) $C_2H_5$ | H | $CH_3$ | $C_2H_5$ | 1.4570 |
| I' | n-$C_3H_7$ | H | $CH_3$ | $C_2H_5$ | 1.4573 |

(1) (2) the stereochemistry of these esters about the double bond $\alpha\beta$ to the cyclopropane ring is (1) 40:60 and (2) 80:20 Z:E.

EXAMPLE 4

A suspension of sodium hydride in oil (0.50 g., approx. 0.0095M NaH) was washed with dry diethyl ether (20 ml.) under nitrogen. Dry dimethylsulphoxide (DMSO) (3.5 ml.) was added and the mixture heated to 80° for 0.5 hours. After cooling, a slurry of n-butyl triphenylphosphonium bromide (3.80 g., 0.0104M) (prepared by reaction of n-butyl bromide with triphenylphosphine) in DMSO (9 ml.) was added with stirring, the remainder of the slurry being washed in with diethyl ether (10 ml.). The mixture was stirred for 0.5 hours and ethyl 3-acetyl-2,2-dimethyl cyclopropane carboxylate (1.0 g., 0.0054M) was added. The mixture was thoroughly shaken and stirred for 24 hours under nitrogen. Ice was added and the mixture acidified with aqueous potassium hydrogen sulphate. After diethyl ether extraction, the organic solution was washed with water, saturated sodium chloride solution, and evaporation of the dried solution ($Na_2SO_4$) yielded a solid which on extraction with petroleum spirit (60°–80°) and evaporation yielded a colourless liquid b.p. 112°–188°/20 mm, 0.52 g, (43%) $n_D$ 1.4573. This liquid was identified by NMR spectroscopy as the compound of formula II where $R^2$=n—$C_3H_7$, $R^3$=H, $R^1$=$CH_3$ and R=$C_2H_5$. (Compound I').

EXAMPLE 5

Chloromethylenetriphenylphosphonium chloride (2.1 g, 0.006M) and dry piperidine (0.51 g, 0.006M), in dry diethyl ether (15 ml) was treated, under nitrogen, with 8% n-butyl lithium in hexane (4.8 ml, [0.388 g, 0.006M]). The mixture was stirred at room temperature for 1.5 hours and t.-butyl (1R)-trans-caronaldehyde (1.27 g, 0.0064M) in dry benzene (5 ml) was added. The mixture was left to stir for 3 days and the solution filtered and the residue washed with dry diethyl ether. The filtrate was washed with 10% $H_2SO_4$, water and evaporation of the dried ($Na_2SO_4$) solvent followed by distillation yielded a colourless liquid b.p. 100°/20 mm. (70%). This was identified by NMR spectroscopy as the ester of formula II where $R^3$=Cl, $R^2$=H, $R^1$=H and R=t.—$C_4H_9$ and was found to have $n_D$ 1.4670. The stereochemistry about the double bond $\alpha\beta$ to the ring was 20:80 Z:E.

The alkyl esters whose preparation is described above in Examples 1 to 5 were then converted into the corresponding 5-benzyl-3-furylmethyl ester by the procedures described below in Examples 6–9.

EXAMPLES 6–7

0.2 mols of sodium were slowly added to a solution of 2 mols of 5-benzyl-3-furylmethyl alcohol in toluene. When the reaction between the sodium and the alcohol to give the sodium alcoholate was complete, a solution containing about 1 molar proportion of the alkyl ester of formula II in toluene was added and the mixture heated under reflux with separation of the methanol or ethanol evolved in the trans-esterification reaction. After the solution had cooled, the desired 5-benzyl-3-furylmethyl ester was recovered in yields of 50–70%, based on the weight of alkyl ester, by chromatography on alumina. The structure of the esters as being in accordance with formula II was confirmed by NMR spectroscopy and gas/liquid chromatography.

The following insecticidal esters were prepared:

| Compound | $R^3$ | $R^2$ | $R^1$ | $n_D$ | |
|---|---|---|---|---|---|
| A | $C_2H_5$ | H | H | 1.5174 | (trans isomer) |
| A cis | $C_2H_5$ | H | H | 1.5347 | ((1R)cis isomer) |
| B | n-$C_3H_7$ | H | H | 1.5177 | |
| C | n-$C_4H_9$ | H | H | 1.5128 | |
| F | H | H | $CH_3$* | 1.5157 | |
| G | $CH_3$ | H | $CH_3$* | 1.5206 | |
| H | $C_2H_5$ | H | $CH_3$* | 1.5180 | |
| I | n-$C_3H_7$ | H | $CH_3$* | 1.5118 | |

Compounds A–I are all compounds of formula II where R=5-benzyl-3-furylmethyl. *These compounds are a mixture of (1RS)-cis-trans-isomers.

Compound A cis was prepared from A' cis by treating with thionyl chloride in benzene to convert A' cis to the acid chloride and then reacting the acid chloride with 5-benzyl-3-furylmethyl alcohol in benzene in the presence of pyridine.

EXAMPLE 8

Methyl 2,2-dimethyl-3-(but-1-enyl)-cyclopropane carboxylate, (prepared as described in Example 2), (2.8 g.) was refluxed for 1 hour with 1.8 g. NaOH in 70 mls. methanol. The reaction mixture was then diluted with water, acidified and extracted with diethyl ether to give 2.01 g. 2,2-dimethyl-3-(but-1-enyl)-cyclopropane carboxylic acid, $n_D$ 1.4719. The acid was then converted into its acid chloride by reaction with thionyl chloride and the acid chloride then esterified by reaction in benzene with an equimolar amount of (±)-allethrolone, (+)-pyrethrolene, 3-benzylbenzyl alcohol or 3-phenoxybenzyl alcohol in the presence of an equimolar amount of pyridine. The reaction mixture was then chromatographed on neutral alumina and the solvent evaporated to give the desired ester. The following insecticidal esters were prepared:

| Compound | $R^2$ | $R^3$ | $R^1$ | R | $n_D$ |
|---|---|---|---|---|---|
| Q | $C_2H_5$ | H | H | (±)-allethronyl | 1.5009 |
| R | $C_2H_5$ | H | H | (+)-pyrethronyl | 1.5159 |
| S | $C_2H_5$ | H | H | 3-benzylbenzyl | 1.5488 |
| T | $C_2H_5$ | H | H | 3-phenoxybenzyl | 1.5439 |

EXAMPLE 9

A mixture of the tertiary butyl ester described in Example 6 (410 mg.) toluene-4-sulphonic acid (47.5 mg.) and dry benzene (15 ml.) were refluxed 2 hours and cooled to give a solution of the corresponding carboxylic acid. Pyridine (163 mg.) and thionyl chloride (213 mg.) wore then added, and the mixture allowed to stand for 2 hours to give the acid chloride. A mixture of substantially equimolar proportions of the acid chloride, 5-benzyl-3-furylmethyl alcohol and pyridine was prepared in dry benzene and the mixture cooled and allowed to stand at room temperature overnight. The mixture was then poured through a column of neutral alumina and eluted with benzene to give a compound of formula II where $R^3$=Cl, $R^2$=H, $R^1$=H and R=5-benzyl-3-furylmethyl. This ester, designated ester K, has $n_D$ 1.5418.

EXAMPLE 10

Triphenyl phosphine (13 g.) was dissolved in dry benzene (60 ml.) and ethyl bromoacetate (8.3 g.) was added dropwise. The solution was heated at 70° for 2 days, and then cooled and filtered. The residue was washed with benzene and dried to give about 16 g. of (ethoxycarbonylmethyl) triphenylphosphonium bromide. The phosphonium salt (10 g.) was dissolved in water (250 ml.) and 5% aqueous sodium hydroxide was added dropwise with stirring until the solution became alkaline to litmus. The resulting precipitate was filtered off, washed with water and dried. Crystallisation from ethyl acetate/petroleum spirit gave (ethoxycarbonyl methylene) triphenyl phosphorane as a colourless solid in about 80% yield.

The phosphorane (3.2 g., 0.0092M) in dry dichloromethane (30 ml.) was added to t.-butyl(1R)transcaronaldehyde (1.5 g., 0.0076M) (from ozonolysis of t.-butyl (+)-trans-chrysanthemic acid) in dichloromethane (30 ml.) with stirring under nitrogen; stirring was continued at room temperature for 2.5 days. The solution was evaporated, and the residue extracted with petroleum spirit (60°-80°) which on evaporation and distillation yielded a colourless liquid b.p. 112°/0.7 mm., 1.60 g. (79%) $n_D$ 1.4666 which was identified by NMR spectroscopy and gas/liquid chromatography as a compound of formula II where $R^3$=carboethoxy, $R^2$=H and R=t.-butyl. (Compound P19/B').

EXAMPLE 11

The procedure described in Example 10 was repeated but replacing the bromoacetic acid ethyl ester by an equivalent weight of bromoacetic acid methyl ester and by bromoacetic acid propyl ester and making any necessary variations in reaction time or temperature during phosphorane formation, to give compounds of formula II where $R^2$=H, R=t.-butyl and $R^3$=carbomethoxy or carbo-n-propoxy, $n_D$ 1.4677 and 1.4723, (compounds P19/A' and P19/C') respectively.

EXAMPLE 12

The procedure described in Example 10 was repeated replacing the bromoacetic acid ethyl ester by an equivalent weight of α-bromopropionic acid ethyl ester and propyl ester. Esters of formula II were obtained where $R^2$=methyl, R=t.-butyl and $R^3$=carboethoxy and carbo-n-propoxy, $n_D$ 1.4658 and 1.4712 (Compounds P19/D' and P19/E') respectively.

EXAMPLE 13 n-Propyl triphenyl phosphonium iodide was prepared by the procedure described in Example 10 replacing the ethyl bromoacetate by n-propyl iodide. The phosphonium iodide (9.5 g.) was then treated under nitrogen with the $NaNH_2$, obtained from 0.5 g. Na in 100 mls. liquid $NH_3$ and the $NH_3$ allowed to evaporate over 2 hours. Benzene (120 mls.) was then added, the mixture refluxed for 15 minutes and 1.08 g. methyl chloroformate in 50 mls dry benzene then added dropwise. The mixture was refluxed a further 10 minutes and then cooled, filtered and the benzene removed to leave a phosphorane of formula:

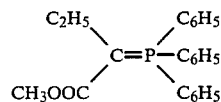

as residue.

The phosphorane was then reacted with t.-butyl caronaldehyde in dichloromethane as described in Example 10 to give a compound b.p. 130°/3 mm., $n_D$ 1.4714 identified as in Example 10 as being of formula II where $R^3$=COOCH$_3$, $R^2$=C$_2$H$_5$, $R^1$=H and R=t.-butyl. (Compound P19/F$^1$).

The above procedure was also repeated replacing the methyl chloroformate by ethyl and n-propyl chloroformate respectively when the following compounds of formula II were obtained.

| | $R^3$ | $R^2$ | $R^1$ | R | b.p. | $n_D$ |
|---|---|---|---|---|---|---|
| P19/G$^1$ | COOC$_2$H$_5$ | C$_2$H$_5$ | H | t-butyl | 114–116°/ 1 mm. | 1.4682 |
| P19/H$^1$ | COOn-C$_3$H$_7$ | C$_2$H$_5$ | H | t-butyl | 120°/ 1 mm. | 1.4683 |

EXAMPLE 14

The compound of formula II where $R^3$=n-propoxy carbonyl, $R^2$=CH$_3$ and R=t.-butyl (0.393 g.) described in Example 12 was refluxed 2 hours with toluene 4-sulphonic acid (47.2 mg.) in benzene (11.5 ml.). The solution was cooled and the resulting acid ($R^3$=n-propoxycarbonyl, $R^2$=CH$_3$, R=H) crystallised out. Dry pyridine (0.127 g., 131 μl.) and thionyl chloride (0.158 g. 96 μl) were added and the mixture left to stand for 2 hours at about 20° when the corresponding acid chloride formed.

A solution of 5-benzyl-3-furylmethyl alcohol (275 mg.) and pyridine (0.105 g., 108 μl.) in benzene (8 ml.) was added and the solution left to stand overnight. The resulting solution was passed through a column of neutral alumina and then evaporated to give 550 mg. of a compound of formula II where $R^3$=n-propoxycarbonyl, $R^2$=CH$_3$ and R=5-benzyl-3-furylmethyl, $n_D$ 1.5125. (Compound P19/E). The structure of the ester as being in accordance with formula II was confirmed by NMR spectroscopy and gas/liquid chromatography.

The following esters were prepared by similar methods.

| Compound | $R^2$ | $R^3$ | $n_D$ |
|---|---|---|---|
| P19/A | H | COOCH$_3$ | 1.5262 |
| P19/B | H | COOC$_2$H$_5$ | 1.5298 |
| P19/C | H | COOn-C$_3$H$_7$ | 1.5278 |
| P19/D | CH$_3$ | COOC$_2$H$_5$ | 1.5235 |
| P19/E | CH$_3$ | COOn-C$_3$H$_7$ | 1.5125 |
| P19/F | C$_2$H$_5$ | COOCH$_3$ | 1.5228 |
| P19/G | C$_2$H$_5$ | COOC$_2$H$_5$ | 1.5193 |
| P19/H | C$_2$H$_5$ | COOn-C$_3$H$_7$ | 1.5190 |

Compounds P19/A to P19/H are all compounds of formula II where R=5-benzyl-3-furylmethyl.

EXAMPLE 15 t.-Butyl-(1R)-trans-caronaldehyde (1.0 g.) (obtained by ozonolysis of the t.-butyl ester of (1R)-transchrysanthemic acid) and triphenyl phosphine (2.65 g.) dissolved in dry carbon tetrachloride (10 ml.) were heated, under nitrogen with stirring, at 60° for 7 hours. The reaction mixture was evaporated under reduced pressure and the residue extracted with diethyl ether (≃30 ml.). The organic extract was washed with water, dried (over Na$_2$SO$_4$) and evaporated. The residue was extracted with petroleum ether (40°-60°) and the solution evaporated and distilled yielding crude product (0.77 g.) (b.p. 100°/1 mm.), which was purified by crystallisation to give t-butyl-(1R)-trans-2,2-dimethyl-3-(2,2-dichlorovinyl) cyclopropane carboxylate m.p. 52°-3° (Compound P21/A').

EXAMPLE 16

Triphenyl phosphine (1.32 g.) was added to a well stirred solution of carbon tetrabromide (0.84 g.) in dry dichloromethane (15 ml.). t-Butyl-(1R)-trans-caronaldehyde (0.5 g.) was added and the solution was stirred overnight at room temperature. After working up as described in Example 15, the crude product was distilled yielding two fractions (1) b.p. 83°-90°/0.7 mm, (0.15 g.), $n_D$ 1.4749 (2) b.p. 90°-107°/0.7 mm, (0.24 g.), $n_D$ 1.4910. The second fraction was shown (glc) to contain ≃95% of the desired t-butyl-(1R)-trans-2,2-dimethyl-3-(2,2-dibromovinyl) cyclopropane carboxylate. (Compound P21/B').

EXAMPLE 17

The t-butyl ester described in Example 15 (280 mg.), was heated at reflux with toluene-4-sulphonic acid (55 mg.) in dry benzene (10 ml.) for 1.5 hour and cooled to give a solution of the corresponding acid. Pyridine (108.5 mg.) and thionyl chloride (126 mg.) were added and the mixture left to stand at room temperature for 2 hours. A solution of pyridine (83.5 mg.) and 5-benzyl-3-furylmethyl alcohol (219 mg.) in dry benzene (5 ml.) was added and the mixture left to stand overnight. After chromatography on neutral alumina, the solution was evaporated to yield 296 mg. of a (1R)trans compound of formula II where $R^3$=Cl, $R^2$=Cl, $R^1$=H and R=5-benzyl-3-furylmethyl. This ester, designated ester P21A, has $n_D$ 1.5403.

The above procedure was repeated with ester P21/B' described in Example 16 to give (1R)trans ester P21/B where $R^2$=$R^3$=Br, $R^1$=H, R=5-benzyl-3-furylmethyl, $n_D$1.5462.

EXAMPLE 18

The conversion of the acid to the acid chloride and subsequent esterification using 5-benzyl-3-furylmethyl alcohol as described in Example 17 was repeated replacing the (1R)-trans acid by other isomers of the acid, and 3-phenoxybenzyl alcohol, 3-benzyl benzyl alcohol, (+)-pyrethrolone, 5-propargyl-2-furylmethyl alcohol, 2,3,4,5-tetrahydrophthalimidomethyl alcohol, α-ethynyl-3-phenoxybenzyl alcohol or (±)-allethrolone were used as the alcohol to give the following esters of formula II.

| Compound | $R^3$ | $R^2$ | $R^1$ | Configuration | m.p.° | $n_D$ |
|---|---|---|---|---|---|---|
| P21C | Cl | Cl | H | (1RS)-trans | 61 | 1.5518 |
| P21D | Cl | Cl | H | (1RS)-cis | 43 | 1.5485 |
| P21E | Cl | Cl | H | (1RS)-cis-trans | 48.58 | 1.5445 |
| P21F | Cl | Cl | H | (1RS)-trans | | 1.5607 |
| P21G | Cl | Cl | H | (1RS)-cis | | 1.5654 |
| P21H | Cl | Cl | H | (1RS)-cis-trans | | 1.5694 |
| P21I | Cl | Cl | H | (1RS)-trans | | 1.5633 |
| P21J | Cl | Cl | H | (1RS)-cis | | 1.5654 |
| P21K | Cl | Cl | H | (1RS)-cis-trans | | 1.5701 |
| P21M | Cl | Cl | H | (1RS)-trans | | 1.5324 |
| P21Q | Cl | Cl | H | (1RS)-trans | | 1.5237 ($n_D^{23}$) |
| P21S | Cl | Cl | H | (1RS)-trans | | 1.5333 ($n_D^{23}$) |
| ME7 | Br | Br | H | (1R)-cis | | 1.5895 |
| ME9 | F | F | H | (1R)-trans | | 1.4889 |
| ME10 | F | F | H | (1R)-cis | | 1.4915 |

In compounds P21C, P21D and P21E, R=5-benzyl-3-furylmethyl, in compounds P21F, P21G and P21H, R is 3-phenoxybenzyl, in compounds P21I, P21J and P21K, R is 3-benzylbenzyl, in P21M, R is (+)-pyrethronyl, in P21Q, R is 5-propargyl-2-furylmethyl, in P21S, R is 3,4,5,6-tetrahydrophthalimidomethyl, in ME7, R is α-ethynyl-3-phenoxybenzyl, and in ME9 and ME10, R is (±)-allethronyl.

The starting acid was prepared by a variant on the conventional chrysanthemic acid synthesis using ethyl diazoacetate in which, in this case, 1,1-dichloro-4-methyl-1,3-pentadiene was reacted with ethyldiazoacetate in the presence of the copper catalyst and the resulting ethyl(1RS)-cis-trans-2,2-dimethyl-3-(2,2-dichlorovinyl)-cyclopropane carboxylate hydrolysed to the free acid. The cis- and trans-isomers can be separated from one another by selective crystallisation from n-hexane in which the cis isomer is more soluble. The isomeric mixture was dissolved in hexane at room temperature and cooled to 0° or −20° C., when the trans-isomer precipitates. This precipitate was ground up, washed with a small volume of hexane at room temperature and the residue recrystallised again from hexane at 0° or −20° C., to give the trans-isomer as a residue. The cis-isomer is recovered from the hexane solution.

EXAMPLE 19 a. 5-Benzyl-3-furylaldehyde

Chromium trioxide (3.00 g.) was added to a stirred solution of pyridine (4.75 g.) in dry methylene chloride (75 ml.), and stirring was continued for 15 minutes. 5-Benzyl-3-furylmethyl alcohol (0.94 g.) was added and the mixture stirred for 15 minutes. The mixture was filtered and the residue washed with ether (100 ml). The filtrate and washings were combined and washed with 5% sodium hydroxide solution (3×50 ml.), 2.5N hydrochloric acid (50 ml.) and 5% sodium carbonate solution (50 ml.) and dried (Na$_2$SO$_4$). Yield=(0.53 g.), b.p. 116°/0.8 mm.Hg, n$_D$=1.5652.

b. (αRS)-Cyano-5-benzyl-3-furylmethyl alcohol

The aldehyde (1) (0.53 g.) was added to a solution of potassium cyanide (0.3 g.) in water (3 ml.) and dioxan (5 ml.) was added to effect solution. The solution was stirred for 10 minutes at 15° C., when 40% sulphuric acid (1 ml.) was added dropwise, stirring being continued for a further 10 minutes. The mixture was extracted with carbontetrachloride (50 ml.) and dried (Na$_2$SO$_4$). Evaporation yielded the product (0.53 g.), n$_D$ 1.5377. (The structure was confirmed by NMR).

c. (αRS)-Cyano-5-benzyl-3-furylmethyl-(1RS)-cis-trans-3-(2,2-dichlorovinyl)-2,2-dimethyl cyclopropane carboxylate (Compound P21/N).

A mixture of the alcohol (265 mg.) prepared as described above, and 80 mg. pyridine in 10 ml. dry benzene was added to 227 mg. of (1RS)-cis-trans-3-(2,2-dichlorovinyl)-2,2-dimethyl cyclopropane carboxylic acid chloride in 10 ml. dry benzene. The resulting mixture was left overnight and then column chromatographed on neutral alumina. Evaporation of solvent gave 0.31 g. of Compound P21/N, n$_D$ 1.5428. (Structure confirmed by NMR).

EXAMPLE 20 a. 3-Phenoxybenzaldehyde

Chromium trioxide (3.00 g.) was added to a stirred solution of pyridine (4.75 g.) in dry methylene chloride (75 ml.), and stirring was continued for a further 15 minutes. 3-Phenoxybenzyl alcohol (1 g.) in methylene chloride (5 ml.) was added, the mixture stirred for a further 15 minutes, decanted and the residue washed with diethyl ether (100 ml.). The filtrate was washed with 5% sodium hydroxide solution (3×50 ml), 2.5 NHCl (50 ml.) and 5% sodium carbonate solution (50 ml.) and dried over Na$_2$SO$_4$ to give 3-phenoxy-benzaldehyde. Alternatively the alcohol can be oxidized using Jones' reagent, a similar yield of aldehyde being obtained.

Yield (0.80 g.), b.p. 126°/0.8 mm.Hg, n$_D$=1.5984.

b. (αRS)-Cyano-3-phenoxybenzyl alcohol

3-Phenoxybenzaldehyde (0.8 g.) was added to a solution of potassium cyanide (0.3 g.) in water (1 ml.) at 15°. Slowly during 10 minutes 40% sulphuric acid (1 ml.) was added dropwise, stirring being continued for a further 15 minutes. The mixture was extracted with carbon tetrachloride (40 ml.); dried (Na$_2$SO$_4$) and evaporated to yield 0.64 g. of (αRS)-α-cyano-3-phenoxybenzyl alcohol. n$_D$=1.5832 (Structure confirmed by MMR). (c) This α-cyano alcohol described above (247 mg.), pyridine (79 mg.) and (1RS)-cis-trans-2,2-dimethyl-3-(2,2-dichlorovinyl)cyclopropane carboxylic acid chloride (227 mg.) were reacted at 20° C., in benzene (20 ml.) solution for 18 hours, which after chromatography on neutral alumina and evaporation of the solvent yielded (αRS)-cyano-3-phenoxybenzyl-(1RS)-cis-trans-3-(2,2-dichlorovinyl)-2,2-dimethyl cyclopropane carboxylate (Compound P21/P) (260 mg.), n$_D$ 1.5561. (Structure confirmed by NMR).

EXAMPLE 21 a. 3-Benzylbenzaldehyde

Benzylbenzyl alcohol (1 g.) was oxidised using the chromium trioxide/pyridine complex as described in Example 20(a) yielding the aldehyde (0.67 g.), b.p. 124° C./0.2 mm, n$_D$20=1.6010.

b. (αRS)-Cyano-3-benzylbenzyl alcohol

The prepared aldehyde (0.67 g.) underwent the reactions described in Example 20(b) to form the required cyanohydrin (0.41 g.), n$_D$20=1.5703.

(αRS)-Cyano-3-benzylbenzyl-(1RS)-cis-trans-(2,2-dichlorovinyl)-2,2-dimethylcyclopropane carboxylate (Compound P21/Q) of n$_D$ 1.5462 was prepared from the alcohol of (b) above and the acid chloride following the procedure of Example 20(c).

EXAMPLE 22 a. 3'-Phenoxybenzyl-3-formyl-2,2-dimethylcyclopropane carboxylate

3-Phenoxybenzyl-(1R)-trans-chrysanthemate (2.0 g.) in methanol (500 g.) at −70° C., was subjected to a stream of ozone for 30 minutes. Nitrogen was passed through the solution and dimethyl sulphide (1.5 g.) added. It was allowed to warm to room temperature and stirred overnight. The solvent was evaporated and acetone (30 ml.) and 30% acetic acid (20 ml.) were added, the solution being allowed to stand for 30 minutes at 80° C. It was poured onto water (200 ml.) and extracted with ether (200 ml.). After washing with sodium carbonate solution the organic solution was dried (Na$_2$SO$_4$) and evaporated to give the title aldehyde. Yield (1.69 g.) n$_D$20=1.5558.

b. The procedure described in Example 15 was repeated using 3'-phenoxybenzyl-3-formyl-2,2-dimethyl cyclopropane carboxylate in place of t.-butyl caronaldehyde to give compound P21F (see Example 18) directly.

EXAMPLE 23

Triphenyl phosphine (13 g.) was dissolved in dry benzene (60 ml.) and methyl bromoacetate (8.3 g.) was added dropwise. The solution was heated at 70° C., for 2 days, and then cooled and filtered. The residue was washed with benzene and dried to give about 16 g. of (methoxycarbonyl methyl)triphenylphosphonium bromide. The phosphonium salt (10 g.) was dissolved in water (250 ml.) and 5% aqueous sodium hydroxide was added dropwise with stirring until the solution became alkaline to litmus. The resulting precipitate was filtered off, washed with water and dried. Crystallisation from ethyl acetate/petroleum spirit gave (methoxycarbonyl methylene) triphenyl phosphorane as a colourless solid in about 80% yield.

(Methoxycarbonylmethyl)triphenylphosphorane (3.34 g.) in methylene chloride (70 ml.) was cooled to −70° C., triethylamine (1.01 g.) was added with stirring followed by chlorine (0.77 g.) in CCl$_4$ (11 mls). Stirring was continued for 30 minutes at this temperature and for 1 hour while the reaction mixture warmed to room temperature. The reaction mixture was washed with water (3×50 ml.), dried over Na$_2$SO$_4$ and evaporated to yield 2.8 g. of chlorinated phosphorane/Ph$_3$P=C(Cl)COOMe.

A mixture of t.-butyl-(1R)trans-caronaldehyde (from ozonolysis of t.-butyl ester of (1R)-trans-chrysanthemic acid) (0.7 g.) and the chlorinated phosphorane (1.3 g.) in 10 ml. dry benzene was refluxed for one hour. After distillation of the benzene, the resulting product was distilled under reduced pressure to give t.-butyl-2,2-dimethyl-3-(2-chloro-2-carbomethoxyvinyl)-cyclopropyl carboxylate, b.p. 110° C./0.4 mm, n$_D^{20}$ 1.4749 (Yield, 0.65 g.).

This compound was designated Compound P24A'.

EXAMPLE 24

The procedure described in Example 23 was repeated replacing the methyl bromoacetate by ethylbromoacetate or propylbromoacetate and by replacing the methylbromoacetate by ethylbromoacetate and replacing chlorine by bromine in the halogenation of the phosphorane step. The following compounds of formula II were obtained.

| Compound | R | R$^3$ | R$^2$ | b.p. | n$_D^{20}$ |
|---|---|---|---|---|---|
| P24B' | t.-butyl | COOC$_2$H$_5$ | Cl | 110–112° C./ 0.4 mm | 1.4883 |
| P24C' | t.-butyl | COOn-C$_3$H$_7$ | Cl | 160–180° C./ 0.8 mm | 1.4688 |
| P24D' | t.-butyl | COOC$_2$H$_5$ | Br | 120–124° C./ 0.04 mm | 1.4830 |

EXAMPLE 25

A mixture of compound P24A' of Example 23 (320 mg.) and toluene-4-sulphonic acid (50 mg.) in dry benzene (10 ml.) were refluxed for approximately 2 hours and then cooled. 2,2-Dimethyl-3-(2-chloro-2-carbomethoxyvinyl)-cyclopropane carboxylic acid was identified in the solution by NMR. Pyridine (111 mg., 114 microliters) and thionyl chloride (132 mg., 80 microliters) were added to the solution of the carboxylic acid and the mixture was left for 3 hours at room temperatures. 2,2-Dimethyl-3-(2-chloro-2-carbomethoxyvinyl)-cyclopropane carboxylic acid chloride was identified in the solution by NMR. A solution of 5-benzyl-3-furylmethyl alcohol (210 mg.) and pyridine (88 mg., 90 microliters) in dry benzene (5 ml.) was added and the mixture left overnight at room temperature. The solution was then run through a column of neutral alumina and eluted with benzene to give 200 mg. of the 5-benzyl-3-furylmethyl ester of 2,2-dimethyl-3-(2-chloro-2-carbomethoxyvinyl)cyclopropane carboxylic acid, n$_D^{20}$ 1.5398. This compound was designated compound P24A.

EXAMPLE 26

The procedure described in Example 25 was repeated using compounds P24B', P24C' and P24D' of Example 24 and the following compounds of formula II were obtained.

| Compound | R$^3$ | R$^2$ | n$_D^{20}$ |
|---|---|---|---|
| P24B | COOC$_2$H$_5$ | Cl | 1.5404 |
| P24C | COOn-C$_3$H$_7$ | Cl | 1.5332 |
| P24D | COOC$_2$H$_5$ | Br | 1.5366 |

The above three compounds are compounds of formula II where R represents 5-benzyl-3-furylmethyl.

EXAMPLE 27

Methyl-(1R)-cis-caronaldehyde was obtained by ozonolysis of methyl (1R)-cis-chrysanthemate. The procedure described in Example 16 was then repeated using 5.3 g. triphenylphosphine, 3.36 g. carbon tetrabromide and 60 mls. dry dichloromethane and 1.5 g. methyl-(1R)-cis-caronaldehyde. The reaction product was then refluxed 3 hours with 9 mls. acetic acid, 6 mls. concentrated HBr and 3 mls. water and then diluted with water and extracted with ether. The organic solution was extracted with dilute sodium hydroxide and this extract acidified and extracted with ether and evaporated to give a residue of (1R)cis-2,2-dimethyl-3-(2,2-dibromovinyl)-cyclopropane carboxylic acid.

The carboxylic acid described above was converted to its acid chloride by reaction with thionyl chloride in pyridine as described in Example 17 and the resulting acid chloride reacted with 3-phenoxybenzyl alcohol in dry benzene in the presence of pyridine as described in Example 17 to give 3-phenoxybenzyl(1R)cis-2,2-dimethyl-3-(2,2-dibromovinyl)cyclopropane carboxylate, m.p. 93°, n$_D$1.5848 (Compound P29A).

The esterification described above was repeated replacing 3-phenoxybenzyl alcohol by (αRS)-cyano-3-phenoxybenzyl alcohol to give (αRS)-cyano-3-phenoxybenzyl(1R)cis-2,2-dimethyl-3-(2,2-dibromovinyl)cyclopropane carboxylate, n$_D$ 1.5732. (Compound P29B). Compound P29B has [α]$_D^{20}$=−1° (C=0.4 in ethanol). N.M.R. peaks associated with the C—H group (carbon atom bearing the α-cyano substituent) γ=3.65 and 3.72 (equal areas).

0.6 grams of the racemate was dissolved in 25 ml hexane and maintained at −20° C. until precipitation of crystals was complete. The crystals were then filtered off and recrystallised from hexane to give (αS)-cyano-3-phenoxybenzyl(1R)cis-2,2-dimethyl-3-(2,2-dibromovinyl)cyclopropane carboxylate in 0.25 g yield. The physical characteristics of this crystalline isomer are as follows:

m.p. 100° C. [α]$_D^{20}$+16° (C=0.4 in ethanol)

N.M.R. Peaks associated with the C—H group (carbon atom bearing the α-cyano substituent) γ=3.65 but no peak at γ=3.72.

The mother liquors were combined and evaporated to dryness to give 0.32 g of the non-crystalline isomer, (αR)-cyano-3-phenoxybenzyl(1R)cis-2,2-dimethyl-3-(2,2-dibromovinyl)cyclopropane carboxylate having the following properties:

n$_D$ 1.5749 [α]$_D^{20}$−15° (C=0.4 in ethanol)

N.M.R. Peaks associated with the C—H bond (carbon atom bearing to the α-cyano group) γ=3.72 with a small peak (20% of the 3.72 peak) at γ=3.65 attributable to the crystalline isomer.

EXAMPLE 28

The esterification procedures described in Example 27 were repeated replacing the (1R)cis-dibromovinyl acid by (1R)trans-2,2-dimethyl-3-(2,2-dibromovinyl)-cyclopropane carboxylic acid (obtained as described in Example 16), (1R)trans-2,2-dimethyl-3-(2,2-dichlorovinyl)-cyclopropane carboxylic acid (prepared as described in Example 15) and (1RS)-cis-trans-2,2-dimethyl-3-(2,2-dichlorovinyl)-cyclopropane carboxylic acid prepared as described in Example 18. The following esters were prepared:

3-phenoxybenzyl(1R)trans-2,2-dimethyl-3-(2,2-dibromovinyl)-cyclopropane carboxylate, $n_D$ 1.5828 (Compound P29C).

(αRS)-cyano-3-phenoxybenzyl(1R)trans-2,2-dimethyl-3-(2,2-dibromovinyl)-cyclopropane carboxylate, $n_D$ 1.5664 (Compound P29D).

(αRS)-cyano-3-phenoxybenzyl(1R)trans-2,2-dimethyl-3-(2,2-dichlorovinyl)-cyclopropane carboxylate $n_D$ 1.5498 (Compound P29E).

(αRS)-cyano-3-phenoxybenzyl(1RS)-cis-trans-2,2-dimethyl-3-(2,2-dichlorovinyl)-cyclopropane carboxylate, $n_D$ 1.5632 (Compound P29F).

(αRS)-cyano-3-phenoxybenzyl(1RS)-cis-2,2-dimethyl-3-(2,2-dichlorovinyl)-cyclopropane carboxylate, $n_D$ 1.5597 (Compound P29G).

(αRS)-cyano-3-phenoxybenzyl(1RS)-trans-2,2-dimethyl-3-(2,2-dichlorovinyl)-cyclopropane carboxylate, $n_D$ 1.5551 (Compound P29H).

(αRS)-cyano-3-phenoxybenzyl(1R)-cis-2,2-dimethyl-3-(2,2-dichlorovinyl)-cyclopropane carboxylate, $n_D$ 1.5622 (Compound P29J).

(αRS)-cyano-3-phenxoybenzyl(1S)-cis-2,2-dimethyl-3-(2,2-dichlorovinyl)-cyclopropane carboxylate, $n_D$ 1.5520 (Compound P29K).

The required isomer of the acid for the last four-mentioned esters was obtained by resolution as described in Example 32.

EXAMPLE 29

(1R)Trans-3-(2,2-difluorovinyl)-2,2-dimethyl-cyclopropane carboxylic acid a. A mixture of freshly distilled, dry, dimethyl formamide (20 ml), triphenylphosphine (7.9 g), methyl (1R)trans-caronaldehyde (3.0 g) and the sodium salt of chlorodifluoro acetic acid (3.6 g) were heated at 90° C. with stirring for 20 hours. Water (60 ml) were then added and the solution extracted with 2×30 ml portions of diethylether. The combined ethereal extracts were washed with water, saturated sodium carbonate solution, saturated sodium chloride solution, and then dried over sodium sulphate and the ether distilled off. Distillation of the residue gave 2.25 g of methyl(1R)-trans-3-(2,2-difluorovinyl)-2,2-dimethyl cyclopropane carboxylate, b.p. 63° C./20 mm, $n_D$ 1.4209.

b. An alkaline solution was prepared by dissolving sodium hydroxide (200 mg) in water (1 ml) and ethanol (10 ml) was added. The methyl ester described above (0.5 g) was stirred into the alkaline solution and the mixture was refluxed for 1 hour. The solvents were removed under reduced pressure and water (30 ml) added. The solution was washed with 2×20 ml portions of diethylether and acidified with concentrated hydrochloric acid. The mixture was extracted with 2×30 ml portions of diethylether, washed with saturated sodium chloride solution, dried over sodium sulphate and the solvents evaporated to leave 410 mg of (1R)-trans-3-(2,2-difluorovinyl)-2,2-dimethyl-cyclopropane carboxylic acid as an oil having $n_D$ 1.4400.

EXAMPLE 30

(1R)-Cis-3-(2,2-difluorovinyl)-2,2-dimethyl-cyclopropane carboxylic acid a. The procedure described in Example 29(a) above was repeated using 1.5 g methyl(1R)-cis-caronaldehyde, 2.92 g triphenylphosphine, 1.2 g sodium chlorodifluoro acetate and 7 ml diemthylformamide. The residue obtained after evaporating the final diethyl ether extracted was itself extracted with 3×40 ml portions of petroleum ether and the petroleum ether evaporated and the residue distilled to give 440 mg of methyl(1R)-cis-3-(2,2-difluorovinyl)-2,2-dimethyl-cyclopropane carboxylate b.p. 74°-78° C./20 mm, $n_D$ 1.41288.

b. The methyl ester obtained above (380 mg) was added to a solution of sodium hydroxide (200 mg) in water (1 ml) and ethanol (10 ml). The mixture was refluxed for 1 hour with stirring and the solvents removed under reduced pressure. Water (50 ml) was then added and the solution washed with 20 ml diethylether, acidified with concentrated hydrochloric acid and extracted with diethyl ether. The ethereal extract was washed wih saturated sodium chloride, dried over sodium sulphate and evaporated to give 290 mg of (1R)-cis-3-(2,2-difluorovinyl)-2,2-dimethyl-cyclopropane carboxylic acid, $n_D$ 1.4456.

EXAMPLE 31

The acids described in Examples 29 and 30 were esterified with 5-benzyl-3-furylmethyl alcohol, 3-phenoxybenzyl alcohol and (αRS)-cyano-3-phenoxybenzyl alcohol by the following procedure. A solution of the acid (110 mg) in benzene (5 ml) was treated with pyridine (50 μl) and thionyl chloride (45 μl) and left to stand for three hours at the end of which time, the acid has been converted into its acid chloride. A solution of 3-phenoxybenzyl alcohol (137 mg) or an equivalent quantity of the other alcohols and pyridine (50 μl) in benzene (5 ml) was added to the acid chloride and the mixture left to stand overnight. The desired ester was recovered from the solution by passing it through a column of neutral alumina and eluting the column with benzene. The eluate was evaporated to leave the ester as an oil, the following results being obtained.

| Compound | Acid | Alcohol | $n_D$ |
| --- | --- | --- | --- |
| P31A | (1R)-trans | 5-benzyl-3-furylmethyl | 1.5142 |
| P31B | (1R)-trans | 3-phenoxybenzyl | 1.5293 |
| P31C | (1R)-trans | (αRS)-cyano-3-phenoxybenzyl | 1.5330 |
| P31D | (1R)-cis | 5-benzyl-3-furylmethyl | 1.5136 |
| P31E | (1R)-cis | 3-phenoxybenzyl | 1.5349 |
| P31F | (1R)-cis | (αRS)-cyano-3-phenoxybenzyl | 1.5355 |

EXAMPLE 32

(1RS)-cis-trans-2,2-dimethyl-3-(2,2-dichlorovinyl)-cyclopropane carboxylic acid, prepared by reacting ethyl diazoacetate with 1,1-dichloro-4-methyl-penta-1,3-diene and hydrolysing the resulting ethyl ester, was separated into the (1RS)-cis and (1RS)-trans isomers by selective crystallisation in n-hexane, in which the cis isomer is more soluble. The substantially pure cis and trans isomers were then resolved into their individual optical isomers by the following procedure.

Resolution of (1RS)-cis-2,2-dimethyl-3-(2,2-dichlorovinyl)-cyclopropane carboxylic acid. The (1RS)-cis acid (14.6 g) in benzene (250 ml), and (+)-α-methylbenzylamine (8.47 g) in benzene (30 ml) were mixed at 50°, allowed to cool to 20° overnight. The precipitate (13.2 g, 58% required isomer) was recrystallised 3 times from benzene to give the (+)-α-methyl benzylamine salt of the (1S)-cis acid (1.7 g) m.p. 135°, $[\alpha]_D-17.1°$ (C, 1.6 in EtOH) was isolated. Repetition, using (−)-α-methylbenzylamine gave, after 3 crystallizations, the (−)-α-methylbenzylamine salt of the (1R)-cis acid (6.1 g) m.p. 147° $[\alpha]_D-26.1°$ (C, 1.9 in EtOH) and from the mother liquors the (−)-α-methylbenzylamine salt of the (1S)-cis acid (3.8 g) m.p. 139° $[\alpha]_D+14.8°$ (C, 2.0 in EtOH).

Each of the four salts was shaken with benzene (50 ml) and 3N HCl (50 ml) and the benzene layer processed to give the resolved acids. Thus were obtained (1S)-cis-2,2-dimethyl-3-(2,2-dichlorovinyl)cyclopropane carboxylic acid (4.6 g) m.p. 90° $[\alpha]_D-26.9°$ (C, 1.7 in CHCl$_3$) and (1R)-cis-2,2-dimethyl-3-(2,2-dichlorovinyl)cyclopropane carboxylic acid (3.9 g) m.p. 90° $[\alpha]_D+27.2°$ (c, 2.1 in CHCl$_3$).

Resolution of (1RS)-trans-2,2-dimethyl-3-(2,2-dichlorovinyl)cyclopropane carboxylic acid The (1RS)-trans acid (15.6 g) in benzene (180 ml and L-(+)-threo-1-p-nitro-phenyl-2-N,N-dimethylaminopropane-1,3-diol (18.0 g) in benzene (180 ml) were mixed at 50° and cooled to 20° during 2 days. The precipitate (14.2 g) was recrystallised 3 times from trichloroethylene to give the L-(+)-threo-1-p-nitrophenyl-2-N,N-dimethylaminopropane-1,3-diol salt of (1S)-trans-2,2-dimethyl-3-(2,2-dichlorovinyl)cyclopropanecarboxylic acid (8.9 g) m.p. 129°–131° $[\alpha]_D+7.4°$ (c, 2.1 in EtOH). Correspondingly D-(−)-threo-1-p-nitrophenyl-2-N,N-dimethylaminopropane-1,3-diol gave the salt with the (1R)-trans acid (9.4 g) m.p. 129°–131°, $[\alpha]_D-7.3°$ (c, 2.0 in EtOH). Decomposition of the salts with 3N HCl as described for the cis acids gave (1S)-trans-2,2-dimethyl-3-(2,2-dichlorovinyl)cyclopropane carboxylic acid (3.8 g) m.p. 68°–73°, $[\alpha]_D-34.6°$ (c, 1.9 in EtOH) and (1R)-trans-2,2-dimethyl-3-(2,2-dichlorovinyl cyclopropane carboxylic acid (4.1 g) m.p. 69°–73°, $[\alpha]_D+33.0°$ (c, 2.0 In EtOH).

The (1R)-cis and (1R)trans acids were converted to their acid chloride and reacted with 3-phenoxybenzyl alcohol by the procedure described in Example 1 to give the 3-phenoxybenzyl ester of (1R)-cis and of (1R)-trans-2,2-dimethyl-3-(2,2-dichlorovinyl)-cyclopropane carboxylic acid, compounds P29L and P29M respectively.

The (1R)-cis acid was also esterified with 5-benzyl-3-furylmethyl alcohol by the same procedure to give compound P29N, 5-benzyl-3-furylmethyl (1R)-cis-2,2-dimethyl-3-(2,2-dichlorovinyl)cyclopropane carboxylate.

The toxicity of these new esters was tested by the procedure described in detail in our above mentioned application and the following results were obtained:

| Compounds | Relative Toxicity | |
|---|---|---|
| | Houseflies | Mustard Beetles |
| 5-benzyl-3-furylmethyl (1R)-trans-chrysanthemate (Bioresmethrin) | 1,000 | 1,000 |
| P29L | 1,600 | 1,400 |
| P29M | 740 | 2,100 |
| P29N | 2,600 | 2,200 |

The toxicity of compounds P29L and P29M relative to bioresmethrin was also determined against the American cockroach, *Periplaneta americana* L. with the following results.

| Compound | Relative Toxicity |
|---|---|
| Bioresmethrin | 100* |
| P29L | 2,100 |
| P29M | 800 |

*LD$_{50}$ = 2.5 µg/insect

EXAMPLE 33

3,4,5,6-Tetrahydrophthalimidomethyl alcohol was esterified by the procedure described in Example 17 using the (1R)trans-isomer of 3-(2,2-difluorovinyl)-2,2-dimethylcyclopropanecarboxylic acid chloride prepared by reacting the acid with thionyl chloride. The resulting ester, designated DP 870 has $n_D^{20}$ 1.5015. The corresponding (1R)cis-isomer was similarly prepared and is designated DP 891. This is a colourless crystalline solid, m.p. 97°–99° C.

These esters were tested for their knock-down effect on houseflies using a modified Kearns & March technique. The basic technique (cf. soap 19 page 101 and 128 (1943)) was modified by using a chamber having two sprayers at each end, each discharging 1 ml of test solvent every 5 seconds. 0.1 ml of a known solution of test compound was introduced into each sprayer and 200 flies were introduced. The test compound was sprayed for 5 seconds and knock-down counts taken at 1 minutes intervals for ten minutes. From these results, KD$_{50}$ values were calculated. For comparative purposes, similar tests were carried out using natural pyrethrin (25% w/w pyrethrum extract) and bioallethrin. The following results were obtained.

| Test Compound | % Concentration giving KD$_{50}$ of 4 minutes |
|---|---|
| DP 870 | 0.04 |
| DP 891 | 0.014 |
| Pyrethrins | 0.032 |
| Bioallethrin | 0.054 |

The knock-down effect against cockroaches was shown in the following tests. The compound under test was dissolved in odourless kerosene and sprayed on male *Blattella germanica* at various concentrations. The KD$_{50}$ for the compounds were calculated to be as follows:

| Test Compound | % Concentration (w/v) giving KD$_{50}$ at 5 minutes |
|---|---|
| DP 870 | 0.0057 |
| Bioallethrin | 0.064 |
| S—Bioallethrin | 0.033 |

The insecticidal activity of DP 870 against houseflies was tested by spraying *M. domestica* in a Kearns and March chamber with a solution of a compound in odourless kerosene, and LD$_{50}$ values calculated. The activity of DP 870 synergised with piperonylbutoxide was also measured and the results compared with the LD$_{50}$ value for compound P21H of Example 18.

| Test Compound | LD$_{50}$ µg/female |
|---|---|
| DP 870 | 0.09 |

-continued

| Test Compound | LD$_{50}$ μg/female |
| --- | --- |
| DP 870 plus piperonyl-butoxide (1:5 w/w) | 0.04 |
| Compound P21H of Example 18 (Permethrin) | 0.022 |

EXAMPLE 34

4-Phenoxybut-2-ynyl(1R)cis-3-(2,2-difluorovinyl)-2,2-dimethylcyclopropane carboxylate 4-Phenoxybut-2-ynol (0.28 g) in benzene (2.8 ml) and pyridine (0.15 g) was treated with a solution of (1R)-cis-3-(2,2-difluorovinyl)-2,2-dimethylcyclopropanecarboxylic acid chloride (0.33 g) in benzene (3 ml) with cooling. After 5 hours, the mixture was filtered through a column of alumina (3 g) and eluted with benzene. Evaporation of the eluate gave the title ester $n_D^{20}$ 1.5121 (Compound ME3).

Similarly prepared were:
4-Phenoxybut-2-ynyl(1R)-trans-3-(2,2-difluorovinyl)-2,2-dimethylcyclopropane carboxylate $n_D^{20}$ 1.5080 (Compound ME4);
4-Phenoxybut-2-ynyl(1RS)-cis,trans-3-(2,2-dichlorovinyl)-2,2-dimethylcyclopropane carboxylate $n_D^{20}$ 1.5362 (Compound ME5);
4-Phenoxybut-2-ynyl(1R)cis-3-(2,2-dibromovinyl)-2,2-dimethylcyclopropane carboxylate, $n_D^{20}$ 1.5730 (Compound ME6).

EXAMPLE 35

2-Benzylcyclopent-2-enone (16.0 g) and recrystallised N-bromosuccinimide (16 g) in dry CCl$_4$ (100 ml) were refluxed until the NBS disappeared completely to form 4-bromo-2-benzylcyclopent-2-enone. When the reaction was complete, the product was filtered and refluxed in the dark with the silver salt of 2,2-dimethyl-3-(2,2-dichlorovinyl)-cyclopropane carboxylic acid (34.6 g) for 5 hours. The reaction mixture was filtered through a column of alumina and eluted with benzene. Distillation of the eluate gave (±)-2-benzylcyclopentenon-4-yl(1RS)-cis,trans-3,(2,2-dichlorovinyl)-2,2-dimethylcyclopropane carboxylate. This ester was designate ME8.

EXAMPLE 36 a. Preparation of 3-benzoylbenzaldehyde

3-Methylbenzophenone (6.0 g), N-bromosuccinimide (10.9 g) and dry carbon tetrachloride (100 ml) were heated at reflux for 8 hours. ($\simeq$70% of dibromide was present). The mixture was cooled, filtered and the filtrate evaporated to yield the crude dibromide.

Sodium hydroxide (2.35 g) in ethanol (30 ml) was heated to boiling with formic acid (2.7 g) and water was added ($\simeq$5 ml) to form a homogeneous solution. This was poured onto the above crude dibromide in ethanol (40 ml) and the whole was refluxed for 48 hours. Concentrated hydrochloric acid (1 ml) was added and refluxing was continued for 1 hour further. The solution was concentrated ($\simeq$30 ml), treated with water and extracted with ether and the ethereal solution washed with 10% sodium carbonate and sodium chloride solutions, dried over sodium sulphate and evaporated. Purification of the crude mixture via the bisulphite complex yielded the pure aldehyde (1.8 g) b.p. 160°-170° C./0.08 mm.

b. 3-Benzoylbenzaldehyde (alternative preparation)

3-Benzoylbenzyl alcohol (2.0 g) in acetone (10 ml) was treated dropwise at 15°-20° C. with chromic acid solution. After stirring for 5 minutes, water (50 ml) was added and the mixture extracted with ether. The ethereal solution was washed with saturated Na$_2$CO$_3$, saturated NaCl, dried (Na$_2$SO$_4$), evaporated and distilled; b.p. 160°-170° C./0.08 mm, (1.1 g).

c. (αRS)-Cyano-3-benzoylbenzyl alcohol

3-Benzoylbenzaldehyde (1.0 g) in dioxan (5 ml) was treated with water (2.5 ml) and sodium cyanide (0.5 g). The whole was cooled below 15° C. and 40% sulphuric acid (1.4 ml) added dropwise (care being taken to ensure that this temperature was not exceeded). Stirring was continued for 1 hour when water (30 ml) was added and the product extracted with methylene chloride and washed with water, saturated NaCl, dried over Na$_2$SO$_4$ and evaporated.

Yield = 1.1 g; $n_D$ = 1.5996.

EXAMPLE 37

3-Benzoylbenzyl alcohol

3-Methylbenzophenone (52 g), N-bromosuccinimide (63 g) and dry carbon tetrachloride (1,000 ml) were heated at reflux for 8 hours when the mixture was cooled, filtered and the filtrate evaporated to yield the crude bromide. Sodium acetate (32.6 g) and acetic acid (300 ml) were added and the whole heated at reflux for 6 hours, poured into water (1,000 ml) and extracted with ether (1,000 ml). The ethereal solution was washed with water (2×300 ml), saturated sodium carbonate solution and saturated sodium chloride solution, dried (Na$_2$SO$_4$), evaporated and fractionally distilled yielding the acetate (10.5 g), b.p. 138°-140° C./1 mm $n_D$ = 1.5789.

Lower boiling fractions containing the corresponding aldehyde were treated with sodium metabisulphite solution to remove the compound combined with the above acetate and refluxed for 2 hours with sodium hydroxide (3.0 g) in methanol (4.0 ml). The solution was poured onto water (200 ml), extracted with ether (2×200 ml) and the ethereal solution washed with saturated NaCl (2×100 ml), dried over Na$_2$SO$_4$, evaporated and distilled to give the required alcohol b.p. 168°-170° C./1 mm (10.0 g) $n_D$ = 1.6165.

EXAMPLE 38

(1R)cis-2,2-dimethyl-3-(2,2-dibromovinyl)-cyclopropane carboxylic acid was prepared by the procedure described in Example 27. A solution of the acid (1 m. mole) in benzene (10 ml) was treated with an equivalent amount of pyridine and thionyl chloride, and the mixture left to stand at room temperature for two hours. A solution of pyridine (98 mg) 3-benzoylbenzyl alcohol (210 mg) and in dry benzene (2 ml) was then added to the solution containing the carboxylic acid chloride and the mixture left to stand overnight. The next morning, the solution was run through a chromatograph column of neutral alumina and the solution containing the ester evaporated to dryness to give 3-benzoylbenzyl(1R)cis-2,2-dimethyl-3-(2,2-dibromovinyl)-cyclopropane carboxylate (400 mg) $n_D^{20}$ 1.5939. This compound is designated P39A.

EXAMPLE 39

The procedure described in Example 38 was repeated but using (1RS)-trans-2,2-dimethyl-3-(2,2-dichlorovinyl)cyclopropane carboxylic acid described in Example 18, (1R)trans and (1R)cis-2,2-dimethyl-3-(2,2-difluorovinyl)cyclopropane carboxylic acid described in Examples 29 and 30 to give:

3-benzoylbenzyl(1RS)-trans-2,2-dimethyl-3-(2,2-dichlorovinyl)-cyclopropane carboxylate, $n_D^{20}$ 1.5722, Compound P39B;

3-benzoylbenzyl(1R)trans-2,2-dimethyl-3-(2,2-difluorovinyl)-cyclopropane carboxylate, $n_D^{20}$ 1.5478: Compound P39C;

3-benzoylbenzyl(1R)-cis-2,2-dimethyl-3-(2,2-difluorovinyl)-cyclopropane carboxylate, $n_D^{20}$ 1.5507, Compound P39D.

EXAMPLE 40

The procedure described in Example 38 was repeated but using, as the alcohol, (αRS)-cyano-3-benzoylbenzyl alcohol prepared as described in Example 36 to give the following esters:

(αRS)-cyano-3-benzoylbenzyl(1R)cis-2,2-dimethyl-3-(2,2-dibromovinyl)-cyclopropane carboxylate, $n_D^{20}$ 1.5800, Compound P39E, (αRS)-cyano-3-benzoylbenzyl(1RS)-trans-2,2-dimethyl-3-(2,2-dichlorovinyl)-cyclopropane carboxylate, $n_D^{20}$ 1.5593, Compound P39F, (αRS)-cyano-3-benzoylbenzyl(1R)-trans-2,2-dimethyl-3-(2,2-difluorovinyl)-cyclopropane carboxylate, $n_D^{20}$ 1.5437, Compound P39G and (αRS)-cyano-3-benzoylbenzyl(1R)-cis-2,2-dimethyl-3-(2,2-difluorovinyl)-cyclopropane carboxylate, $n_D^{20}$ 1.5450, Compound P39H.

Acaricidal activity has been measured by injecting solutions of test compound P39E into engorged female ticks, *Boophilus microplus*, Biarra strain and the ability of the female to lay eggs 14 days after injection determined. The results are exposed as a percent of inhibition of egg laying ability compared to untreated control ticks. The following results were obtained:

| Compound | % Inhibition Concentration of test compound | | |
|---|---|---|---|
|  | 10 mg/ml | 1 mg/ml | 0.1 mg/ml |
| P39E | 100 | 90 | 0 |

Experiments to compare the relative toxicity (LD$_{50}$) of compound P39E with certain related compounds have been carried out towards both *Ephestia kuhniella* and *Venturia canescens* so that the relative toxicity to the two species can be calculated. The ratio of the selective toxicity to Ephestia compared to Venturia shows a measure of the selectivity of the agent and the higher this selectivity, the more effective is the compound in killing Ephestia without killing its parasite Venturia. The selectivities found were as follows:

| Compound | | Selectivity |
|---|---|---|
| Compound P39E |  | 7.9 |
| 3-Phenoxybenzyl-(1R)-trans-2,2-dimethyl-3-(2,2-dichlorovinyl)cyclopropanecarboxylate | (Compound P29M of Example 32) | 2.8 |
| 3-Phenoxybenzyl(1R)-cis-2,2-dimethyl-3-(2,2-dichlorovinylcyclopropanecarboxylate | (Compound P29L of Example 32) | 2.3 |
| (αS)-cyano-3-phenoxybenzyl-(1R)-cis-2,2-dimethyl-3-(2,2-dibromovinyl)cyclopropanecarboxylate | (S) isomer of Compound P29B of Example 27 | 3.6 |

These results show a very marked and quite unexpected selectivity in favour of compound P39E.

EXAMPLE 41

3-Phenoxybenzyl(1RS)-trans-2,2-dimethyl-3-(2,2-dichlorovinyl)cyclopropane carboxylate (1RS)-Trans-2,2-dimethyl-3-(2,2-dichlorovinyl)-cyanopropane carboxylic acid (1.0 g, 0.0048M), m-phenoxybenzyl alcohol (1.0 g, 0.0050M) and para-toluene sulphonic acid (0.01 g) in toluene (100 ml) were refluxed with a Dean and Stark take-off for 36 hours. On cooling, the solution was extracted with 5% aqueous sodium bicarbonate (2×50 ml), then water (2×50 ml), dried over anhydrous sodium sulphate and evaporated in vacuo. The residue was passed down an acid washed alumina column using petroleum ether (b.p. 80°–100° C.) as eluant. On evaporation of the solvent, this yielded the title compound as a colourless oil which crystallised on standing.

The following formulations are given to illustrate the way in which the insecticidal compounds of the invention can be applied to insects or environments susceptible to insect attacks.

FORMULATION 1

| Oil-based liquid spray for household insects | |
|---|---|
| active compound | 0.015% w/v |
| 25% Pyrethrum Extract | 0.25% |
| Piperonyl butoxide | 0.5% |
| Antioxidant | 0.1% |
| Odourless light oil solvent e.g. xylene to make 100 vols. | |

FORMULATION 2

| Water-based liquid spray concentrate for mosquito control | |
|---|---|
| active compound | 0.25% w/v |
| Piperonyl butoxide | 1.0% |
| Non-ionic emulsifier | 0.25% |
| Antioxidant | 0.1% |
| Water to make | 100 vols. |

This concentrate should be diluted 1:80 v/v with water before spraying.

FORMULATION 3

| Aerosol | |
|---|---|
| active compound | 0.05% w/w |
| 25% Pyrethrum Extract | 0.8% |
| Piperonyl butoxide | 1.5% |
| Odourless petroleum distillate (b.p. 200–265°) | 17.338% |
| Propellant, e.g. a mixture of equal quantities of trichloromonofluoromethane and dichlorodifluoromethane | 80.0% |
| Perfume | 0.2% |
| Antioxidant | 0.1% |

FORMULATION 4

| Mosquito coil | |
|---|---|
| active compound | 0.25% w/w |
| Tabu powder (also known as pyrethrum marc) | 30.0% |
| Filler(s), e.g. wood flour, powdered leaves or nut shells | 68.75% |

-continued

| Mosquito coil | |
|---|---|
| Brilliant Green | 0.5% |
| p-Nitrophenol | 0.5% |

FORMULATION 5

| Emulsifiable concentrate | |
|---|---|
| active compound | 1.5% w/w |
| Non-ionic emulsifier | 25.0% |
| Xylene | 73.4% |
| Antioxidant | 0.1% |

This concentrate may then be diluted at the rate of 30 mls. to 4½ liters of water prior to use.

FORMULATION 6

| General purpose powder for household, garden, livestock or grain storage use | |
|---|---|
| active compound | 0.05% w/w |
| Tropital (the synergist piperonyl-bis-2-[2'-n-butoxyethoxy]ethyl acetal) | 0.25% |
| Antioxidant, e.g. butyl hydroxy toluene or butyl hydroxy anisole | 0.03% |
| Filler | 99.67% |

The insecticidal acitivity of the esters of the invention was assessed against houseflies and mustard beetles using the following techniques:

HOUSEFLIES (MUSCA DOMESTICA)

Female flies were treated on the thorax with a one microliter drop of insecticide dissolved in acetone. Two replicates of 15 flies were used at each dose rate and 6 dose rates were used per compound under test. After treatment, the flies were maintained at a temperature of 20° C.±1° and kill was assessed 24 and 48 hours after treatment. $LD_{50}$ values were calculated in micrograms of insecticide per fly and relative toxicities were calculated from the inverse ratios of the $LD_{50}$ values. (see Sawicki et al, Bulletin of the World Health Organization, 35,893, (1966) and Sawicki et al, Entomologia and Exp. Appl. 10, 253, (1967)).

MUSTARD BEETLES (PHAEDON COCHLEARIAE FAB)

Acetone solutions of the test compound were applied ventrally to adult mustard beetles using a micro drop applicator. The treated insects were maintained for 48 hours after which time kill is assessed. Two replicates of 40 to 50 mustard beetles were used at each dose level and 3 to 4 dose levels were used for each compound. Again, $LD_{50}$ values were calculated and relative toxicities were calculated for the inverse ratios of $LD_{50}$ (see Elliott et al, J. Sci. Food Agric. 20, 561, (1969)).

Relative toxicities were calculated by comparison with 5-benzyl-3-furylmethyl(1R)-trans-chrysanthemate which is one of the most toxic chrysanthemate esters known to houseflies and mustard beetles, its toxicity being about 24 times that of allethrin to houseflies and 65 times that of allethrin to mustard beetles.

The following relative toxicities were obtained.

| Compound | Relative Toxicity Houseflies | Mustard Beetles |
|---|---|---|
| 5-benzyl-3-furylmethyl (1R)-trans-chrysanthemate | 1000 | 1000 |
| Pyrethrin I | 12 | 1600 |
| Bioallethrin | 60 | 20 |
| A | 1700 | 2000 |
| B | 630 | 890 |
| C | 270 | 420 |
| F | 21 | — |
| G | 18 | — |
| H | <7 | 10 |
| I | <7 | <10 |
| K | 1300 | 1600 |
| Q | 60 | 69 |
| R | 30 | 300 |
| S | 120 | 170 |
| T | 240 | 300 |
| P19A | 91 | 100 |
| P19B | 67 | 320 |
| P19C | 24 | 40 |
| P19D | 290 | 440 |
| P19E | 290 | 500 |
| P19F | 130 | 360 |
| P19G | 300 | 500 |
| P19H | 20 | 50 |
| P21A | 2500 | 2700 |
| P21B | 1100 | 1900 |
| P21C | 1000 | 2200 |
| P21D | 1200 | 1700 |
| P21E | 700 | 1800 |
| P21F | 400 | 790 |
| P21G | 680 | 780 |
| P21H | 660 | 740 |
| P21I | 170 | 420 |
| P21J | 360 | 350 |
| P21K | 340 | 350 |
| P21M | 19 | 370 |
| P21N | 100 | 2000 |
| P21P | 1300 at least | 5000 |
| P24A | 82 | 310 |
| P24B | 150 | 310 |
| P24C | 53 | 120 |
| P24D | 450 | 290 |
| P29A | 2200 | 1600 |
| P29B | 10000 | 11000 |
| P29B (crystalline isomer) | 23000 | 14000 |
| P29B (non-crystalline isomer) | 3500 | 4000 |
| P29C | 1100 | 4000 |
| P29D | 4100 | 5200 |
| P29E | 3900 | 3100 |
| P29F | 1700 | — |
| P29G | 3800 | 2400 |
| P29H | 1800 | 750 |
| P29J | 11000 | 4200 |
| P29K | 140 | 130 |
| P29L | 1600 | 1400 |
| P29M | 740 | 2100 |
| P29N | 2600 | 2200 |
| ME3 | 150 | 30 |
| ME4 | 60 | 70 |
| ME5 | 300 | 40 |
| ME6 | 390 | 50 |
| P31A | 3900 | 1900 |
| P31B | 620 | 270 |
| P31C | 840 | 730 |
| P31D | 2300 | 1300 |
| P31E | 1800 | 850 |
| P31F | 1200 | 2200 |
| P39A | 50 | 830 |
| P39B | 10 | 590 |
| P39C | 6 | 50 |
| P39D | 20 | 500 |
| P39E | 330 | 2200 |
| P39F | 80 | 600 |
| ME7 | 1100 | 5000 |
| ME8 | 50 | 265 |
| ME9 | 50 | 50 |
| ME10 | 40 | 30 |

The relative toxicity of compounds P21Q and P21S were measured against houseflies by the turntable method, they were found to have toxicities of 13 mg/100 ml and 200 mg/100 ml respectively and against German cockroaches, by the topical application method, they were found to have toxicities of 6.78 γ/insect and 5.08 γ/insect respectively. These figures are to be compared with 200-300 mg/100 ml and 0.8 to 1.4 γ/insect respectively for natural pyrethrin. Mammalian toxicity of certain esters of the invention has been determined in rats with the following results:

| Compound | $LD_{50}$ (mg/kg) to rats | |
|---|---|---|
| | oral | intravenous |
| Pyrethrin I | 260-420 | 2-5 |
| 5-benzyl-3-furylmethyl (1R)-trans chrysanthemate | >8000 | 340 |
| A | 800-1000 | 120 |
| P21E | 40 | 5 |
| P21C | >400 | 26-33 |

The insecticidal activity and mammalian toxicity of certain esters of (1RS)-trans-2,2-dimethyl-3-(2,2-dichlorovinyl)-cyclopropane carboxylic acid has been tested in a further series of experiments with the following results:

| R | Insecticidal activity | | Mammalian toxicity $LD_{50}$ in μg | |
|---|---|---|---|---|
| | Houseflies*[1] | German Cockroaches*[2] | oral acute $LD_{50}$ mg/kg Rats | Mice |
| —CH$_2$— (m-phenoxyphenyl) | 10.5 mg/100 ml. | 0.83 γ/insect | >300 | >300 |
| —(allethrolone type)—CH$_2$—CH=CH$_2$ | 55 mg/100 ml. | 4.2 γ/insect | — | — |
| —CH$_2$—(furyl)—CH$_2$—C≡CH | 13 mg/100 ml. | 6.7 γ/insect | 300 | approximately 300 |
| —CH$_2$—(furyl)—CH$_2$—phenyl | 4.5 mg/100 ml. | 0.54 γ/insect | — | 100 |
| Pyrethrin: 200-300 mg/100 ml. | 5-benzyl-3-furyl-methyl (1RS)-cis-trans-chrysanthemate. 0.62 γ/insect Pyrethrin: 0.8-1.4 γ/insect | | Pyrethrin 130 | |

*[1] turn table method
*[2] topical application method

The synergisability of certain esters of the invention has been determined in tests in which the $LD_{50}$ of the insecticide in μg. per female fly was determined by the above described methods in untreated flies and in flies pretreated with 2 μg. per fly of the synergist sesamex (2-(3,4-methylene dioxyphenoxy)-3,6,9-trioxa undecane). The following results were obtained

| | $LD_{50}$ | | |
|---|---|---|---|
| Active compound | active compound only | active compound + synergist | Approx. Synergistic factor |
| 5-benzyl-3-furyl methyl (1R)-trans-chrysanthemate | 0.0054 | 0.00057 | 9.4 |
| 5-benzyl-3-furyl methyl (1RS)-cis-trans-chrysanthemate | 0.010 | 0.00079 | 13 |
| P21C | 0.0065 | 0.00033 | 19 |
| P21D | 0.0058 | 0.00046 | 12 |
| P21F | 0.013 | 0.00033 | 39 |
| P21G | 0.0083 | 0.00037 | 22 |
| A[(1R)-trans-(3-cis-but-1-enyl)-isomer] | 0.0042 | 0.00033 | 13 |
| A[(1R)-cis-(3-cis but-1-enyl)-isomer] | 0.0074 | 0.0012 | 6 |

By repeating the above synergisability test but pretreating flies instead with 5 micrograms per fly of the synergist Sesamex 3 hours before applying the pyrethroid, the following results were obtained:

| | $LD_{50}$ in μg | | |
|---|---|---|---|
| Active Compound | Active compound only | Active compound (flies pretreated with synergist) | Approx. synergist factor |
| P21P | 0.0073 | 0.00088 | 8.3 |
| P29B (S) isomer | 0.0016 | 0.00023 | 7 |

The insecticidal activity of the compounds of the invention may also be synergised by formulation with other compounds known to be capable of synergising natural pyrethrin and synthetic pyrethroids. Such synergists include piperonyl butoxide (3,4-methylenedioxy-6-propylbenzyl butyl-diethylene glycol ether); Tropital [piperonyl-bis-2-(2'-n-butoxyethoxy)ethyl acetal); sulphoxide [1,2-methylenedioxy-4-(2-(octylsulphinyl)-propyl)-benzene]; propylisome (di-n-propyl-2-methyl-6,7-methylenedioxy-1,2,3,4-tetrahydronaphthalene-3,4-dicarboxylate) and MCK264 [N-(2-ethylhexyl)-[2,2,1]-5-heptene-2,3-dicarboximide]. These synergists are desirably present in a ratio of 1:1 to 50:1 with respect to the pyrethroid, preferably 1:1 to 10:1.

Topical application of pyrethroids alone and in combination with synergist gave the following $LD_{50}$ results in micrograms with female *Musca domestica*:

| Active compound | $LD_{50}$ (μg) Active compound only | $LD_{50}$ (μg) Active compound + piperonyl butoxide (1:5) | $LD_{50}$ (μg) Active compound + Tropital (1:5) |
| --- | --- | --- | --- |
| P21H | 0.031 | 0.018 | 0.019 |
| P21E | 0.044 | 0.022 | |
| A (trans) | 0.034 | 0.015 | |

We claim:

1. A compound of the general formula II:

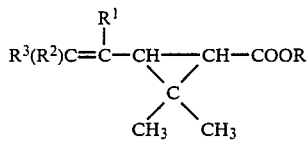

II wherein:
$R^1$ represents hydrogen;
$R^2$ represents halogeno;
$R^3$ represents hydrogen;
R represents a group of formula:

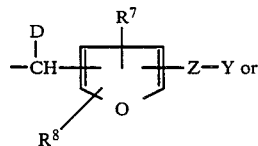

III or

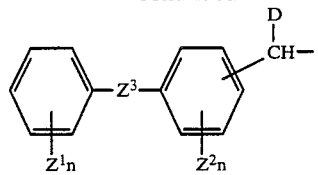

VI wherein:
Z represents $CH_2$;
Y represents an aryl group which is unsubstituted or substituted in the ring by at least one lower alkyl group;
$R^7$ and $R^8$ each represent hydrogen or a lower alkyl group;
D represents H or CN;
$Z^3$ represents O, $CH_2$ or CO;
$Z^1$ and $Z^2$ independently represent chlorine or a methyl group;
n=0, 1 or 2.

2. A compound according to claim 1 wherein R represents:
   (a) a 3-furylmethyl group of formula III wherein $R^7$ and $R^8$ each represent hydrogen or a methyl group, and Y represents a phenyl group which is unsubstituted or substituted in the ring by a methyl group; or
   (b) a substituted benzyl group of formula IV where $Z^1$ and $Z^2$ each represent hydrogen and $Z^3$ represents O or $CH_2$.

3. A compound according to claim 1 wherein the hydrogen atoms at $C_1$ and $C_3$ on the cyclopropane ring are substantially completely in the trans configuration or in the cis configuration.

4. An optically active compound according to claim 3 in the form of a (1R)cis isomer or a (1R)trans isomer.

5. A compound according to claim 1 in the form of a (1RS)-cis trans isomer mixture.

6. A compound according to claim 1 wherein the $R^2$ halogen is chlorine or bromine.

7. A compound according to claim 1 wherein R is 5-benzyl-3-furylmethyl or 3-phenoxy-benzyl.

8. A compound according to claim 1 which is the 5-benzyl-3-furylmethyl ester of 2,2-dimethyl-3-(2-chloro-vinyl)cyclopropane carboxylic acid.

9. A pesticidal composition comprising a pesticidally effective amount of a compound according to claim 1 together with a diluent or carrier.

10. A composition according to claim 9 including a pyrethrin synergist.

11. A composition according to claim 9 including natural pyrethrin or a component thereof or another synthetic pyrethroid.

12. A method of pest control which comprises applying to a pest or an environment susceptible to pest attack a pesticidally effective amount of a compound according to claim 1.

* * * * *